United States Patent
Blum et al.

(10) Patent No.: US 7,077,519 B2
(45) Date of Patent: Jul. 18, 2006

(54) SYSTEM, APPARATUS, AND METHOD FOR CORRECTING VISION USING AN ELECTRO-ACTIVE LENS

(75) Inventors: Ronald D. Blum, Roanoke, VA (US); Dwight P. Duston, Laguna Niguel, CA (US); Dan Katzman, Givat Ela (IL)

(73) Assignee: e-Vision, LLC, Roanoke, VA (US)

( * ) Notice: Subject to any disclaimer, the term of this patent is extended or adjusted under 35 U.S.C. 154(b) by 0 days.

(21) Appl. No.: 10/627,828

(22) Filed: Jul. 25, 2003

(65) Prior Publication Data

US 2004/0056986 A1    Mar. 25, 2004

Related U.S. Application Data

(63) Continuation of application No. 09/602,013, filed on Jun. 23, 2000, now Pat. No. 6,619,799.

(60) Provisional application No. 60/161,363, filed on Oct. 26, 1999, provisional application No. 60/150,564, filed on Aug. 25, 1999, provisional application No. 60/150,545, filed on Aug. 25, 1999, provisional application No. 60/147,813, filed on Aug. 10, 1999, provisional application No. 60/143,626, filed on Jul. 14, 1999, provisional application No. 60/142,053, filed on Jul. 2, 1999.

(51) Int. Cl.
*G02C 7/02* (2006.01)

(52) U.S. Cl. .......................... 351/159; 351/41

(58) Field of Classification Search ............ 351/159, 351/41, 44, 168, 161, 163–165, 169, 176–177, 351/205, 209
See application file for complete search history.

(56) References Cited

U.S. PATENT DOCUMENTS

| | | | |
|---|---|---|---|
| 2,437,642 A | 3/1948 | Henroteau |
| 2,576,581 A | 11/1951 | Edwards |
| 3,161,718 A | 12/1964 | de Luca |
| 3,245,315 A | 4/1966 | Marks et al. |
| 3,614,215 A | 10/1971 | Mackta |
| 3,738,734 A | 6/1973 | Tait et al. |
| 4,174,156 A | 11/1979 | Glorieux |
| 4,181,408 A | 1/1980 | Senders |
| 4,190,330 A | 2/1980 | Berreman |
| 4,264,154 A | 4/1981 | Peterson |
| 4,279,474 A | 7/1981 | Belgorod |
| 4,300,818 A | 11/1981 | Schachar |
| 4,373,218 A | 2/1983 | Schachar |
| 4,395,736 A | 7/1983 | Fraleux |
| 4,418,990 A | 12/1983 | Gerber |

(Continued)

FOREIGN PATENT DOCUMENTS

EP          0 154 962 A2        9/1985

(Continued)

OTHER PUBLICATIONS

M. Anderson, "Adaptive Optics: Liquid Crystals Lower the Cost of Adaptive Optics", *Laser Focus World*, pp. 1-3, Dec. 1999.

(Continued)

*Primary Examiner*—Jordan M. Schwartz
(74) *Attorney, Agent, or Firm*—Pearl Cohen Zedek Latzer, LLP

(57) ABSTRACT

An electro-active spectacle lens is disclosed. The disclosed lens includes a first lens optic. The disclosed lens also includes a first electro-active zone positioned in a cooperative relationship with the first lens optic. In certain embodiments, the electro-active lens includes a range finder positioned in a cooperative relationship with the electro-active lens.

16 Claims, 21 Drawing Sheets

U.S. PATENT DOCUMENTS

| | | | |
|---|---|---|---|
| 4,457,585 A | 7/1984 | DuCorday | |
| 4,466,706 A | 8/1984 | Lamothe, II | |
| 4,529,268 A | 7/1985 | Brown | |
| 4,564,267 A | 1/1986 | Nishimoto | |
| 4,572,616 A | 2/1986 | Kowel et al. | |
| 4,577,928 A | 3/1986 | Brown | |
| 4,601,545 A | 7/1986 | Kern | |
| 4,609,824 A | 9/1986 | Munier et al. | |
| 4,712,870 A | 12/1987 | Robinson et al. | |
| 4,756,605 A | 7/1988 | Okada et al. | |
| 4,772,094 A | 9/1988 | Sheiman | |
| D298,250 S | 10/1988 | Kildall | |
| 4,787,733 A | 11/1988 | Silva | |
| 4,795,248 A | 1/1989 | Okada et al. | |
| 4,818,095 A | 4/1989 | Takeuchi | |
| 4,836,652 A | 6/1989 | Oishi et al. | |
| 4,880,300 A | 11/1989 | Payner et al. | |
| 4,904,063 A | 2/1990 | Okada et al. | |
| 4,907,860 A | 3/1990 | Noble | |
| 4,919,520 A | 4/1990 | Okada et al. | |
| 4,927,241 A | 5/1990 | Kuijk | |
| 4,929,865 A | 5/1990 | Blum | |
| 4,930,884 A | 6/1990 | Tichenor et al. | |
| 4,945,242 A | 7/1990 | Berger et al. | |
| 4,952,788 A | 8/1990 | Berger et al. | |
| 4,958,907 A | 9/1990 | Davis | |
| 4,961,639 A | 10/1990 | Lazarus | |
| 4,968,127 A | 11/1990 | Russell et al. | |
| 4,981,342 A | 1/1991 | Fiala | |
| 4,991,951 A | 2/1991 | Mizuno et al. | |
| 5,015,086 A | 5/1991 | Okaue et al. | |
| 5,030,882 A | 7/1991 | Solero | |
| 5,050,981 A | 9/1991 | Roffman | |
| 5,066,301 A | 11/1991 | Wiley | |
| 5,073,021 A | 12/1991 | Marron | |
| 5,076,665 A | 12/1991 | Petersen | |
| 5,091,801 A | 2/1992 | Ebstein | |
| 5,108,169 A | 4/1992 | Mandell | |
| 5,114,628 A | 5/1992 | Höfer et al. | |
| 5,130,856 A | 7/1992 | Tichenor et al. | |
| 5,142,411 A | 8/1992 | Fiala | |
| 5,171,266 A | 12/1992 | Wiley et al. | |
| 5,182,585 A | 1/1993 | Stoner | |
| 5,184,156 A | 2/1993 | Black et al. | |
| 5,200,859 A | 4/1993 | Payner et al. | |
| 5,208,688 A | 5/1993 | Fergason et al. | |
| 5,229,885 A | 7/1993 | Quaglia | |
| 5,239,412 A | 8/1993 | Naka et al. | |
| D342,063 S | 12/1993 | Howitt et al. | |
| 5,306,926 A | 4/1994 | Yonemoto | |
| 5,324,930 A | 6/1994 | Jech, Jr. | |
| D350,342 S | 9/1994 | Sack | |
| 5,352,886 A | 10/1994 | Kane | |
| 5,359,444 A | 10/1994 | Piosenka et al. | |
| 5,375,006 A | 12/1994 | Haas | |
| 5,382,986 A | 1/1995 | Black et al. | |
| 5,386,308 A | 1/1995 | Michel et al. | |
| 5,412,439 A * | 5/1995 | Horn | 351/45 |
| 5,440,357 A | 8/1995 | Quaglia | |
| 5,443,506 A | 8/1995 | Gurabet | |
| 5,451,766 A | 9/1995 | Van Berkel | |
| 5,488,439 A | 1/1996 | Weltmann | |
| 5,522,323 A | 6/1996 | Richard | |
| 5,608,567 A | 3/1997 | Grupp | |
| 5,615,588 A | 4/1997 | Gottschald | |
| 5,654,786 A | 8/1997 | Bylander | |
| 5,682,223 A | 10/1997 | Menezes et al. | |
| RE35,691 E | 12/1997 | Theirl et al. | |
| 5,712,721 A | 1/1998 | Large | |
| 5,728,155 A | 3/1998 | Anello et al. | |
| 5,739,959 A | 4/1998 | Quaglia | |
| 5,777,719 A | 7/1998 | Williams et al. | |
| 5,815,233 A | 9/1998 | Morokawa et al. | |
| 5,815,239 A | 9/1998 | Chapman et al. | |
| 5,861,936 A | 1/1999 | Sorenson | |
| 5,894,363 A * | 4/1999 | Yamada et al. | 359/251 |
| 5,900,720 A | 5/1999 | Kallman et al. | |
| 5,949,521 A | 9/1999 | Williams et al. | |
| 5,953,098 A | 9/1999 | Lieberman et al. | |
| 5,980,037 A | 11/1999 | Conway | |
| 6,086,204 A | 7/2000 | Magnante | |
| 6,095,651 A | 8/2000 | Williams et al. | |
| 6,145,987 A | 11/2000 | Baude et al. | |
| 6,305,802 B1 | 10/2001 | Roffman et al. | |
| 6,317,190 B1 * | 11/2001 | Winarski et al. | 349/200 |
| 6,325,508 B1 | 12/2001 | Decreton et al. | |
| 6,339,459 B1 * | 1/2002 | Ichikawa et al. | 349/95 |
| 6,437,925 B1 | 8/2002 | Nishioka | |
| 6,464,363 B1 | 10/2002 | Nishioka et al. | |
| 6,554,425 B1 | 4/2003 | Roffman et al. | |
| 6,609,794 B1 | 8/2003 | Levine | |
| 6,616,275 B1 | 9/2003 | Dick et al. | |
| 6,616,279 B1 | 9/2003 | Davis et al. | |
| 6,626,532 B1 | 9/2003 | Nishioka et al. | |
| 6,631,001 B1 | 10/2003 | Kuiseko | |
| 6,682,195 B1 | 1/2004 | Dreher | |
| 6,774,871 B1 * | 8/2004 | Birdwell | 345/48 |

FOREIGN PATENT DOCUMENTS

| | | |
|---|---|---|
| EP | 0 233 104 A1 | 8/1987 |
| EP | 0 237 365 A | 9/1987 |
| GB | 2169417 A | 7/1986 |
| GB | 2170613 A | 8/1986 |
| JP | 55-076323 | 6/1980 |
| JP | 62-209412 * | 9/1987 |
| JP | 1-237610 | 9/1989 |
| WO | WO 98/27863 | 7/1998 |
| WO | WO 03/050472 A1 | 6/2003 |
| WO | WO 03/068059 A2 | 8/2003 |
| WO | WO 2004/008189 A1 | 1/2004 |
| WO | WO 2004/015481 A1 | 2/2004 |
| WO | WO 2004/034095 A2 | 4/2004 |

OTHER PUBLICATIONS

"Focusing by Electrical Modulation of Refraction in a Liquid Crystal Cell"; Stephen T. Kowel et al., *Applied Optics*, vol. 23, No. 2, Jan. 15, 1984, pp. 278-289.

"Computer Vision Syndrome—The Eyestrain Epidemic"; Robert A. Davis, O.D., *Review of Optometry*, Sep. 15, 1997, pp. 80-88.

"The Use of Yoked Base-Up and Base-In Prism for Reducing Eye Strain at the Computer"; Stuart M. Lazarus, O.D., *Journal of the American Optometric Association*, Apr. 1996, pp. 204-208.

*Eyecare Business*, Oct. 1997 (entire issue).

"Vision Through a Liquid-Crystal Spatial Light Modulator"; Larry N. Thibos et al., *Inpress*, Adaptive Optics Conference, Durham, United Kingdom, 1999.

"Requirements for Segmented Spatial Light Modulators for Diffraction-Limited Imaging Through Aberrated Eyes"; Larry N. Thibos et al., *Inpress*, Adaptive Optics Conference, Durham, United Kingdom, 1999.

"Use of Liquid-Crystal Adaptive-Optics to Alter the Refractive State of the Eye"; Larry N. Thibos et al., *Optometry and Vision Science*, vol. 74, No. 7, Jul. 1997.-

"Electronics Spectacles for the 21st Century", *Indiana Journal of Optometry*, vol. 2, No. 1, 1999.

"Profile: Larry N. Thibos, Ph.D. and Donald Miller, Ph.D.", *Indiana Journal of Optometry*, vol. 2, No. 1, pp. 5-10, 1999.

"Control Optimization of Spherical Modal Liquid Crystal Lenses"; A. F. Naumov and G. D. Love, *Optics Express*, vol. 4, No. 9, Apr. 26, 1999, pp. 344-352.

"Liquid Crystal Adaptive Lenses with Modal Control"; A. F. Naumov and M. Yu Loktev, *Optics Letters*, vol. 23, No. 13, Jul. 1, 1998, pp. 992-994.

"Liquid Lenses Eye Commercial Breakthrough" (Internet Article under "Optics.org"); from *Opto & Laser*, Nov. 2003.

* cited by examiner

SYSTEM, APPARATUS, AND METHOD FOR CORRECTING VISION USING AN ELECTRO-ACTIVE LENS

This application is a continuation of U.S. patent application Ser. No. 09/602,013, filed Jun. 23, 2000, now U.S. Pat. No. 6,619,799 which claims priority to the following U.S. Provisional Patent Applications, all of which are hereby incorporated by reference in their entirety:

Ser. No. 60/142,053, titled "Electro-Active Spectacles", filed Jul. 2, 1999;

Ser. No. 60/143,626, titled "Electro-Active Spectacles", filed Jul. 14, 1999;

Ser. No. 60/147,813, titled "Electro-Active Refraction, Dispensing, & Eyewear", filed Aug. 10, 1999;

Ser. No. 60/150,545, titled "Advanced Electro-Active Spectacles", filed Aug. 25, 1999;

Ser. No. 60/150,564, titled "Electro-Active Refraction, Dispensing, & Eyewear", filed Aug. 25, 1999; and Ser. No. 60/161,363, titled "Comprehensive Electro-Active Refraction, Dispensing, & Eyewear" filed Oct. 26, 1999.

This invention relates to the following which are incorporated herein by reference in their entirety:

"System, Apparatus and Method for Correcting Vision Using an Electro-Active Lens" U.S. application Ser. No. 10/627,828 filed concurrently herewith;

"System, Apparatus, and Method for Correcting Vision Using Electro-Active Spectacles", U.S. application Ser. No. 09/602,012, filed Jun. 23, 2000, now U.S. Pat. No. 6,517,203;

"Method for Refracting and Dispensing Electro-Active Spectacles", U.S. application Ser. No. 09/602,014, filed Jun. 23, 2000, now U.S. Pat. No. 6,491,394; and "System, Apparatus, and Method for Reducing Birefringence", U.S. application Ser. No. 09/603,736, filed Jun. 23, 2000, now U.S. Pat. No. 6,491,391.

FIELD OF THE INVENTION

The present invention relates to the field of vision correction, and, more particularly, to a system, apparatus, and method for correcting vision using an electro-active lens.

BRIEF DESCRIPTION OF THE DRAWINGS

The invention will be more readily understood through the following detailed description, with reference to the accompanying drawings, in which.

DETAILED DESCRIPTION

Figure 1:
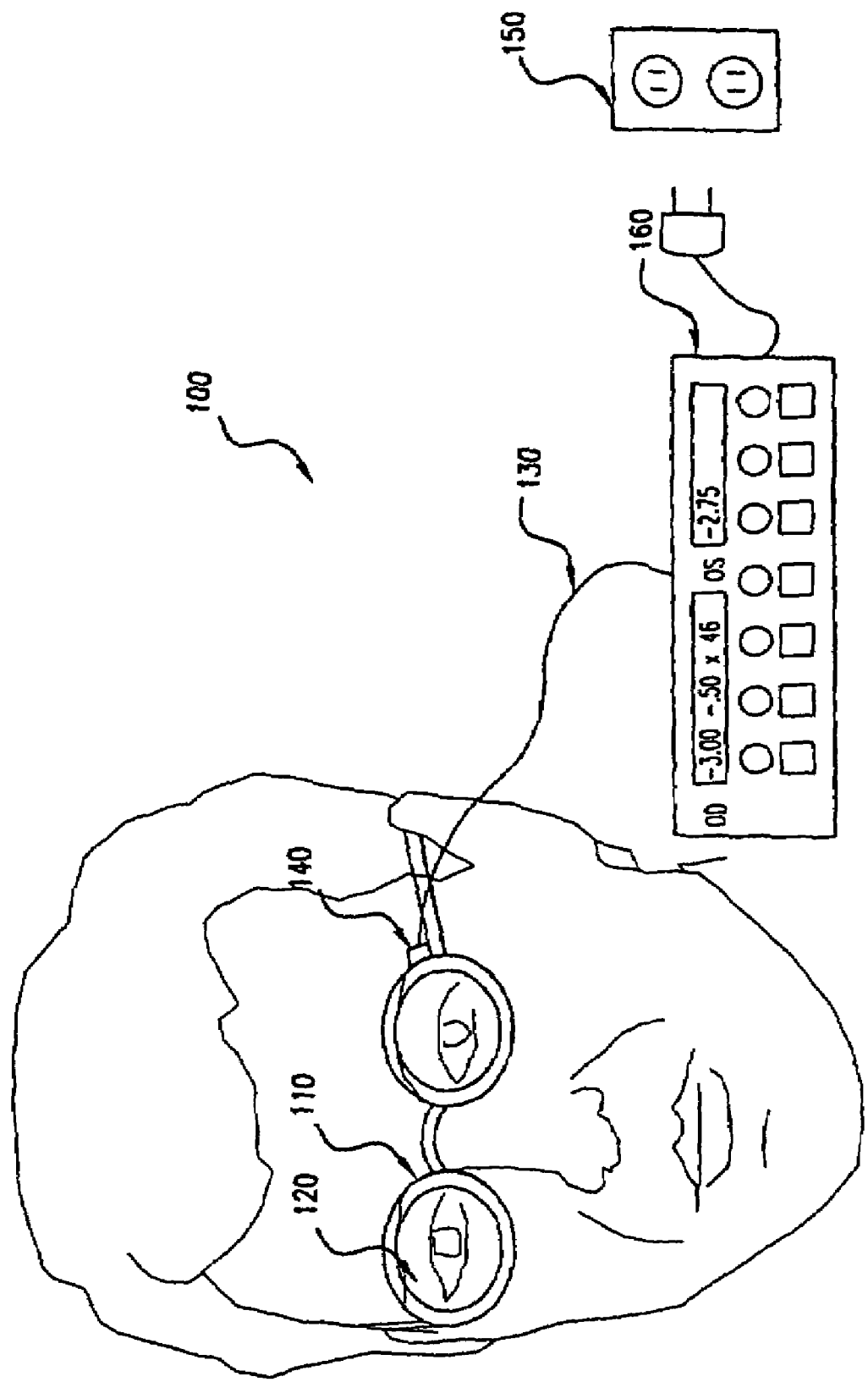
FIG. 1 is a perspective view of an embodiment of an electro-active phoropter/refractor system 100.

In 1998, there were approximately 92 million eye examinations performed in the United States alone. The vast majority of these examinations involved a thorough check for eye pathology both internal and external, analysis of muscle balance and binocularity, measurement of the cornea and, in many cases, the pupil, and finally a refractive examination, which was both objective and subjective.

Refractive examinations are performed to understand/diagnose the magnitude and type of the refractive error of one's eye. The types of refractive error that are currently able to be diagnosed & measured, are myopia, hyperopia, astigmatism, and presbyopia. Current refractors (phoropters) attempt to correct one's vision to 20/20 distance and near and, in some cases, 20/15 distance vision can be achieved; however, this is by far the exception.

It should be pointed out that the theoretical limit to which the retina of one's eye can process and define vision is approximately 20/10. This is far better than the level of vision which is currently obtained by way of both today's refractors (phoropters) and conventional spectacle lenses.

What is missing from these conventional devices is the ability to detect, quantify and correct for non-conventional refractive error, such as aberrations, irregular astigmatism, or ocular layer irregularities. These aberrations, irregular astigmatism, and/or ocular layer irregularities may be as a result of one's visual system or as a result of aberrations caused by conventional eyeglasses, or a combination of both.

Therefore, it would be extremely beneficial to have a means for detecting, quantifying, and correcting one's vision as close to 20/10 or better as possible. Furthermore, it would be beneficial to do this in a very efficient and user friendly manner.

The present invention utilizes a novel approach in detecting, quantifying and correcting one's vision. The approach involves several innovative embodiments utilizing an electro-active lens. Furthermore, the invention utilizes a novel approach towards the selection, dispensing, activating, and programming of electro-active eyewear.

For example, in one inventive embodiment, a novel electro-active phoropter/refractor is utilized. This electro-active phoropter/refractor utilizes far fewer lens components than today's phoropters and is a fraction of the overall size and/or weight of today's phoropters. In fact, this exemplary inventive embodiment consists of only a pair of electro-active lenses housed in a frame mounting that provides, either through its own structural design and/or by way of a network of conductive wires, electrical power needed to enable the electro-active lenses to function properly.

To assist with understanding certain embodiments of the invention, explanations of various terms are now provided. In some situations, these explanations are not necessarily intended to be limiting, but, should be read in light of the examples, descriptions, and claims provided herein.

An "electro-active zone" can include or be included in an electro-active structure, layer, and/or region. An "electro-active region" can be a portion and/or the entirety of an electro-active layer. An electro-active region can be adjacent to another electro-active region. An electro-active region can be attached to another electro-active region, either directly, or indirectly with, for example, an insulator between each electro-active region. An electro-active layer can be attached to another electro-active layer, either directly, or indirectly with, for example, an insulator between each electro-active layer. "Attaching" can include bonding, depositing, adhering, and other well-known attachment methods. A "controller" can include or be included in a processor, a microprocessor, an integrated circuit, an IC, a computer chip, and/or a chip. A "refractor" can include a controller. An "auto-refractor" can include a wave front analyzer. "Near distance refractive error" can include presbyopia and any other refractive error needed to be corrected for one to see clearly at near distance. "Intermediate distance refractive error" can include the degree of presbyopia needed to be corrected an intermediate distance and any other refractive error needed to be corrected for one to see clearly at intermediate distance. "Far distance refractive error" can include any refractive error needed to be corrected for one to see clearly at far distance. "Near distance" can be from about 6 inches to about 24 inches, and more preferably from about 14 inches to about 18 inches. "Intermediate distance" can be from about 24 inches to about 5 feet. "Far distance" can be any distance between about 5 feet and infinity, and more preferably, infinity. "Conventional refractive error" can include myopia, hyperopia, astigmatism, and/or presbyopia. "Non-conventional refractive error" can include irregular astigmatism, aberrations of the ocular system, and any other refractive error not included in conventional refractive error. "Optical refractive error" can include any aberrations associated with a lens optic.

In certain embodiments, a "spectacle" can include one lens. In other embodiments, a "spectacle" can include more than one lens. A "multi-focal" lens can include bifocal, trifocal, quadrafocal, and/or progressive addition lens. A "finished" lens blank can include a lens blank that has finished optical surface on both sides. A "semi-finished" lens blank can include a lens blank that has, on one side only, a finished optical surface, and on the other side, a non-optically finished surface, the lens needing further modifications, such as, for example, grinding and/or polishing, to make it into a useable lens. "Surfacing" can include grinding and/or polishing off excess material to finish a non-finished surface of a semi-finished lens blank.

FIG. 1 is a perspective view of an embodiment of electro-active phoropter/refractor system 100. Frames 110 contain electro-active lens 120, which are connected via a network of conductive wires 130 to an electro-active lens controller 140 and to an electrical power source 150.

In certain embodiments, the temples (not shown in FIG. 1) of frames 110 contain batteries or power sources such as, for example, a micro-fuel cell. In other inventive embodiments, the temple or temples of frame 110 possess the needed electrical components so that a power cord is plugged directly into an electrical outlet and/or the electro-active refractor's controller/programmer 160.

Still in other inventive embodiments, the electro-active lenses 120 are mounted in a housing assembly which is suspended so one could simply position one's face properly in order to look through the electro-active lenses while being refracted.

While the first inventive embodiment utilizes only a pair of electro-active lenses, in certain other inventive embodiments, multiple electro-active lenses are used. Still in other inventive embodiments, a combination of conventional lenses and electro-active lenses are utilized.

Figure 2:
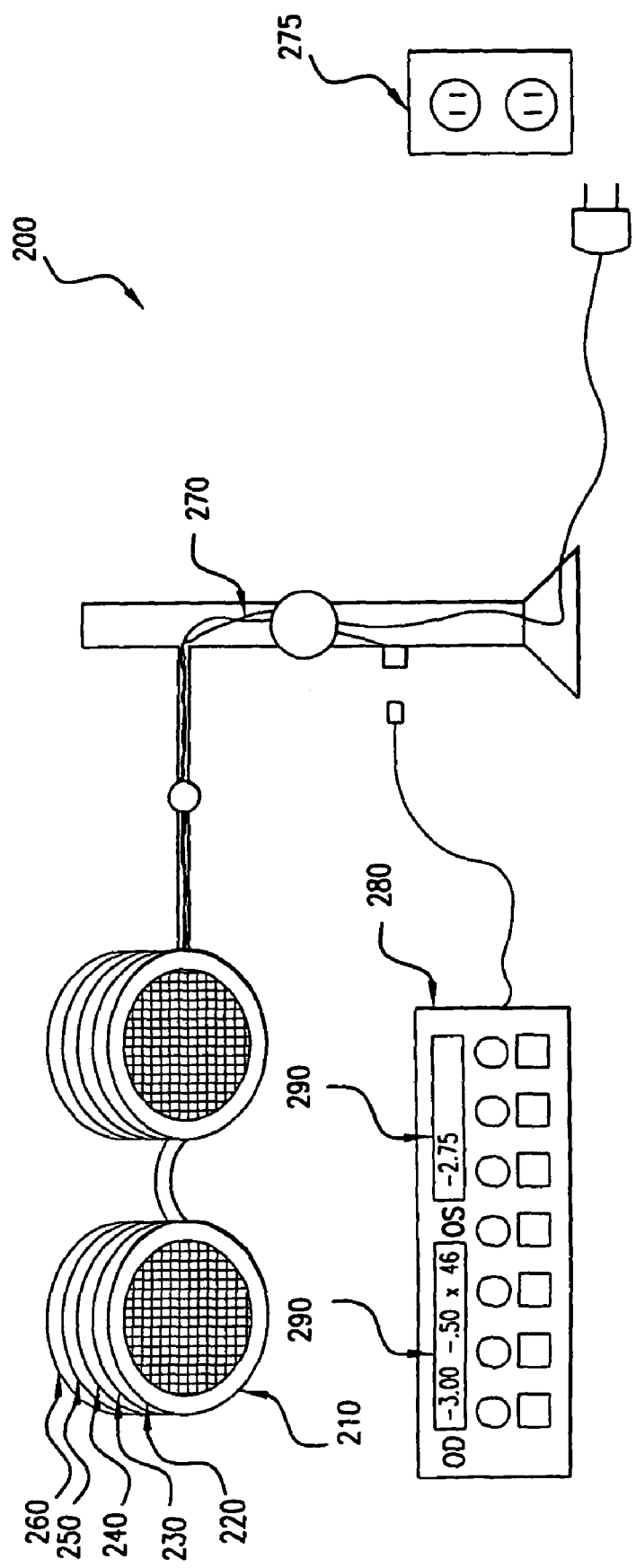
FIG. 2 is a diagrammatic view of an embodiment of another electro-active phoropter/refractor system 200.

FIG. 2 is a diagrammatic view of an exemplary embodiment of an electro-active refractor system 200 that includes housing assembly 210 that contains at least one electro-active lens 220 and several conventional lenses, specifically, diffractive lens 230, prismatic lens 240, astigmatic lens 250, and spherical lens 260. A network of conductive wires 270 connects the electro-active lens 220 to a power source 275 and to a controller 280, that provides a prescription display 290.

In each inventive embodiment where multiple electro-active lenses and/or a combination of conventional and electro-active lenses are utilized, the lenses can be used to test one's vision in a random and/or non-random one-at-a-time sequence. In other inventive embodiments, two or more lenses are added together giving a total corrective power in front of each eye as needed.

The electro-active lenses, which are utilized in both the electro-active phoropter and the electro-active eyewear, are comprised of either a hybrid and/or non-hybrid construction. In a hybrid construction, a conventional lens optic is combined with an electro-active zone. In a non-hybrid construction, no conventional lens optic is used.

Figure 3:
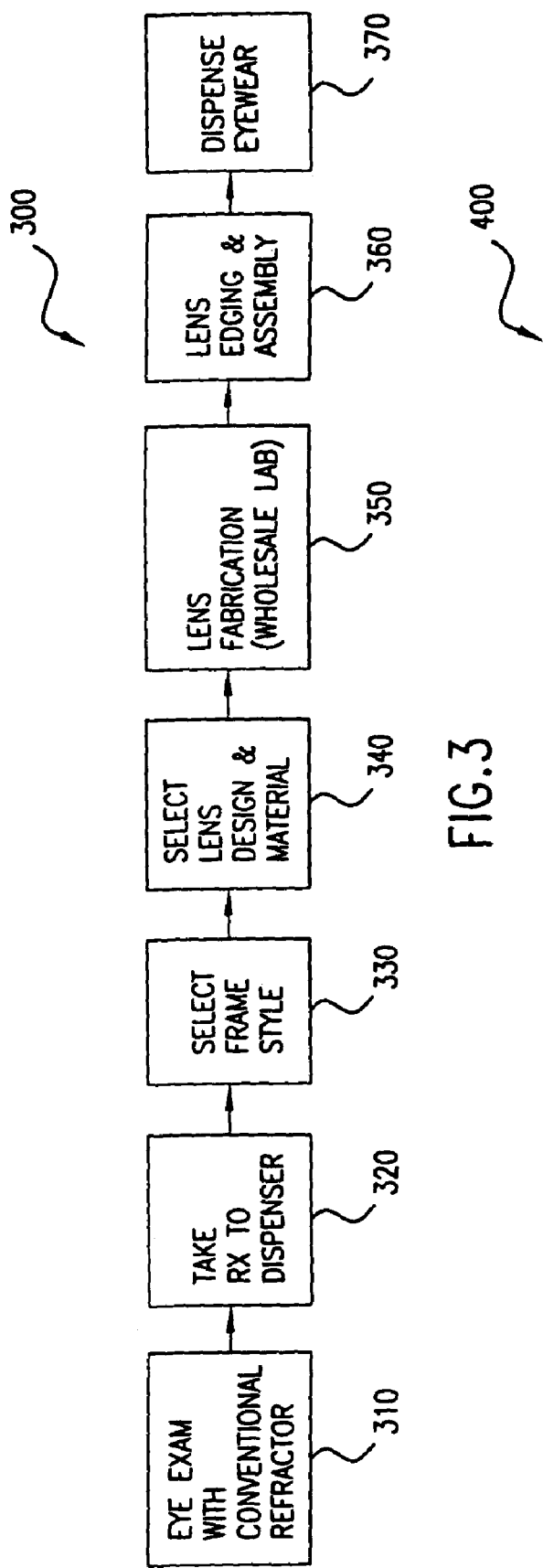
FIG. 3 is a flow diagram of a conventional dispensing practice sequence 300.

As discussed above, the invention differs from today's conventional dispensing practice sequence 300, which is shown as a flow diagram in FIG. 3. As shown at steps 310 and 320, traditionally an eye examination involving a conventional refractor is followed by obtaining one's prescription and taking that prescription to a dispenser. Then, as shown at steps 330 and 340, at the dispenser one's frames and lens are selected. As shown at step 350 and 360, the lenses are fabricated, edged, and assembled into the frames. Finally, at step 370, the new prescription eyeglasses are dispensed and received.

Figure 4:
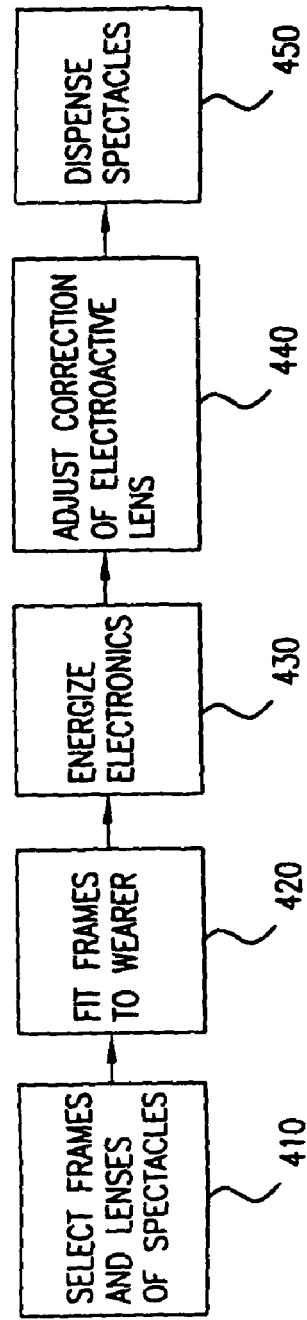
FIG. 4 is a flow diagram of an embodiment of dispensing method 400.

As shown in the flow diagram of FIG. 4, in an exemplary embodiment of one inventive dispensing method 400, at step 410 the electro-active eyewear is selected by or for the wearer. At step 420, the frames are fitted to the wearer. With the wearer wearing the electro-active eyewear, at step 430, the electronics are controlled by the electro-active phoropter/refractor control system which in most cases is operated by an eyecare professional and/or technician. However, in certain inventive embodiments, the patient or wearer can actually operate the control system and thus, control the prescription of their own electro-active lenses. In other inventive embodiments, both the patient/wearer and the eyecare professional and/or technician work with the controller together.

At step 440, the control system, whether operated by the eyecare professional, technician, and/or the patient/wearer, is utilized to select both objectively or subjectively the best correcting prescription for the patient/wearer. Upon selecting the proper prescription to correct the patient/wearer's vision to it's optimal correction, the eyecare professional or technician then programs the patient's/wearer's electro-active eyewear.

In one inventive embodiment, the selected prescription is programmed into an electro-active eyewear controller, and/or one or more controller components, prior to the selected electro-active eyewear being disconnected from the electro-active phoropter/refractor's controller. In other inventive embodiments the prescription is programmed into the selected electro-active eyewear at a later time.

In either case the electro-active eyewear is selected, fitted, programmed, and dispensed at step 450 in a totally different sequence than conventional eyeglasses are today. This sequence allows for improved manufacturing, refracting and dispensing efficiencies.

Via this inventive method, the patient/wearer literally can select their eyewear, wear them while the testing of their vision is taking place, and then have them programmed for the correct prescription. In most cases, but not all, this is done before the patient/wearer leaves the examination chair, thus, ensuring the total fabrication and programming accuracy of the patient's final prescription, as well as the accuracy of the eye refraction itself. Finally, in this inventive embodiment the patient can literally wear their electro-active eyeglasses when they get up out of the examination chair and proceed out of the eyecare professional's office.

It should be pointed out that other inventive embodiments allow for the electro-active phoropter/refractor to simply display or print out the patient or wearer's best corrected prescription which is then filled in much the same manner as in the past. Currently the process involves taking a written prescription to a dispensing location where electro-active eyewear (frames and lenses) are sold and dispensed.

Still in other inventive embodiments the prescription is sent electronically, for example, via the Internet, to a dispensing location where electro-active eyewear (frames and lenses) are sold.

In the case where the prescription is not filled at the point where the eye refraction is performed, in certain inventive embodiments an electro-active eyewear controller, and/or one or more controller components, is either programmed and installed into the electro-active eyewear, or directly programmed while installed in the electro-active eyewear, following the refraction. In the case where nothing is added to the electro-active eyewear, the electro-active eyewear controller, and/or one or more controller components, is an intricate built-in part of the electro-active eyewear and does not need to be added at a later time.

Figure 27:
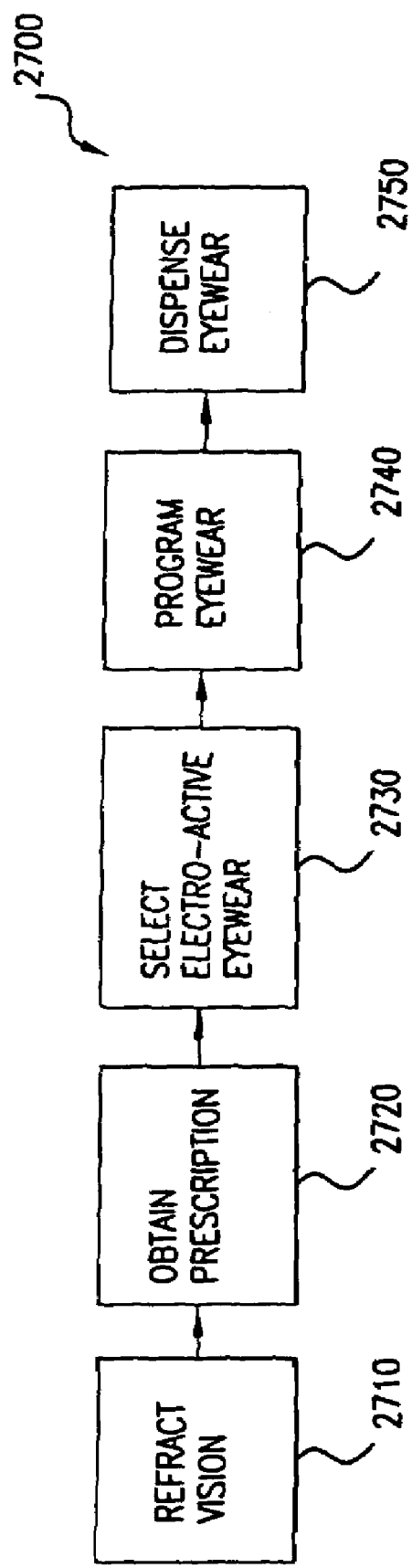
FIG. 27 is a flow diagram of an embodiment of dispensing method 2700.

FIG. 27 is a flow diagram of an embodiment of another inventive dispensing method 2700. At step 2710, the vision of the patient is refracted using any method. At step 2720, the prescription for the patient is obtained. At step 2730, the electro-active eyewear is selected. At step 2740, the electro-active eyewear is programmed with the wearer's prescription. At step 2750, the electro-active eyewear is dispensed.

Figure 5:
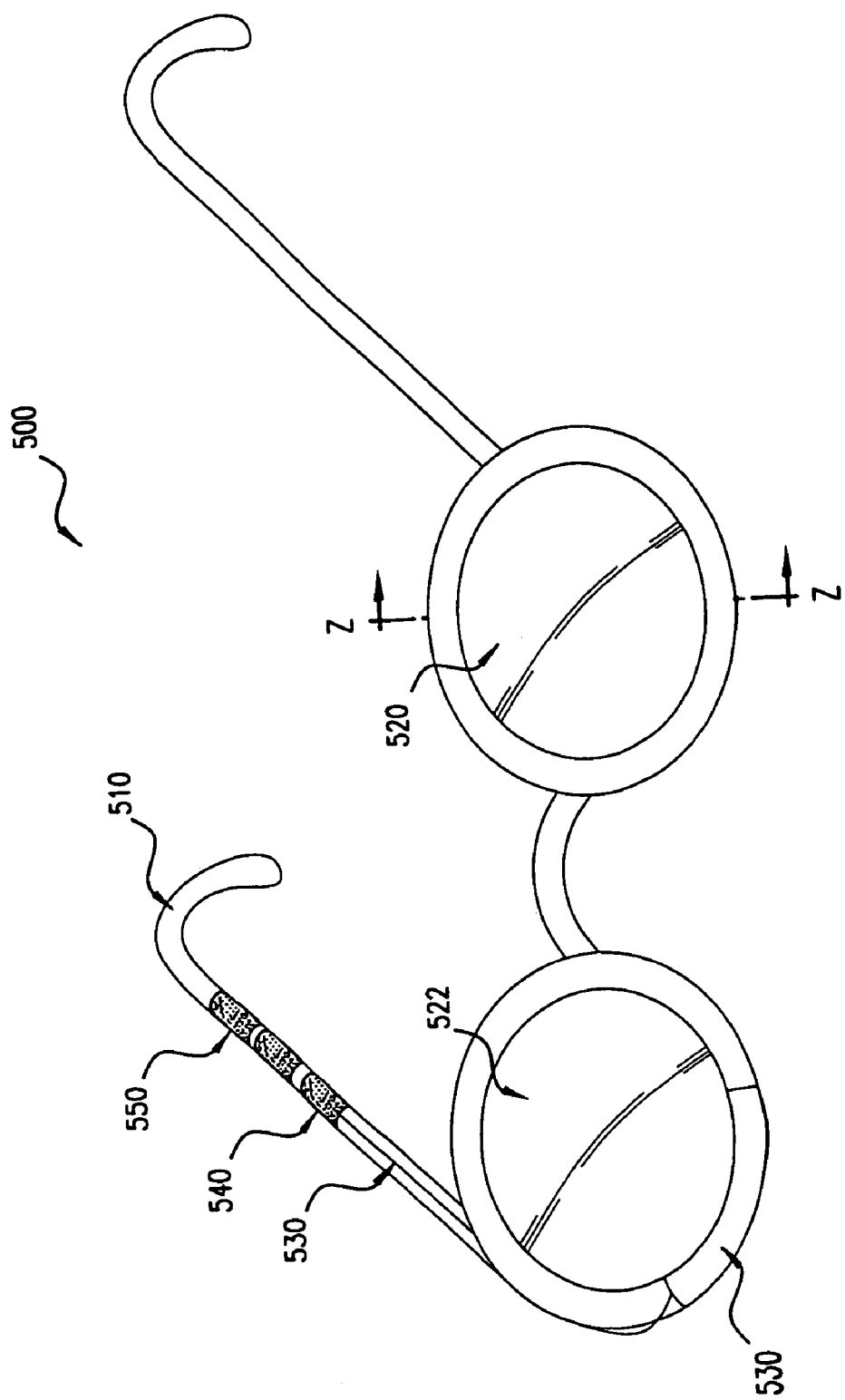
FIG. 5 is a perspective view of an embodiment of electro-active eyewear 500.

FIG. 5 is a perspective view of another inventive embodiment of the electro-active eyewear 500. In this illustrative example, frames 510 contain generic electro-active lenses 520 and 522 that are electrically coupled by connecting wires 530 to electro-active eyewear controller 540 and power source 550. Section line Z—Z divides generic electro-active lens 520.

Controller 540 acts as the "brains" of the electro-active eyewear 500, and can contain at least one processor component, at least one memory component for storing instructions and/or data for a specific prescription, and at least one input/output component, such as a port. Controller 540 can perform computational tasks such as reading from and writing into memory, calculating voltages to be applied to individual grid elements based on desired refractive indices, and/or acting as a local interface between the patient/user's eyewear and the associated refractor/phoropter equipment.

In one inventive embodiment, controller 540 is pre-programmed by the eyecare specialist or technician to meet the patient's convergence and accommodative needs. In this embodiment, this pre-programming is done on controller 540 while controller 540 is outside the patient's eyewear, and controller 540 is then inserted into the eyewear after the examination. In one inventive embodiment, controller 540 is a "read-only" type, supplying the voltage to grid elements to obtain the necessary array of refractive indices to correct the vision for a specific distance. As the patient's prescription changes, a new controller 540 must be programmed and inserted into the eyewear by the specialist. This controller would be of a class of ASIC's, or application specific integrated circuits, and its memory and processing commands permanently imprinted.

In another inventive embodiment, the electro-active eyewear controller may be originally programmed by the eyecare specialist or technician when first dispensed, and later the same controller, or a component thereof, can be reprogrammed to provide a different correction, as the patient's needs change. This electro-active eyewear controller may be extracted from the eyewear, placed in the refractor's controller/programmer (shown in FIGS. 1 and 2) and reprogrammed during the examination, or reprogrammed, in situ, by the refractor without removal from the electro-active eyewear. The electro-active eyewear controller in this case could, for example, be of a class of FPGA's, or field programmable gate array architecture. In this inventive embodiment the electro-active eyewear controller may be permanently built into the eyewear and require only an interface link to the refractor which issues the reprogramming commands to the FPGA. Part of this link would include external AC power to the electro-active eyewear controller provided by an AC adapter embedded in the refractor/phoropter or in its controller/programmer unit.

In another inventive embodiment, the electro-active eyewear acts as the refractor, and the external equipment operated by the eyecare specialist or technician consists of merely a digital and/or analog interface to the electro-active eyewear's controller. Thus, the electro-active eyewear controller can also serve as the controller for the refractor/phoropter. In this embodiment, the necessary processing electronics are available to alter the array of grid voltages to the electro-active eyewear and reprogram the electro-active eyewear controller with this data after the optimal correction for the user is empirically determined. In this case, the patient reviews the eye charts through his/her own electro-active eyewear during the examination and may be unaware that as he/she is selecting the best corrective prescription, the controller in their electro-active eyewear is simultaneously being reprogrammed electronically.

Another innovative embodiment utilizes an electronic auto-refractor that can be used as a first step and/or in combination with the electro-active refractors (shown in FIGS. 1 and 2) such as by way of example, but not limited to Humphrey's Auto-refractor & Nikon's Auto-refractor which have been developed or modified to provide feed back which is compatible and programmed for use with the invention's electro-active lenses. This innovative embodiment is used to measure one's refractive error, while the patient or wearer is wearing his or her electro-active spectacles. This feedback is fed automatically or manually into a controller and/or programmer, which then calibrates, programs or reprograms the controller of the user/wearer's electro-active spectacles. In this innovative embodiment, one's electro-active spectacles can be re-calibrated as needed without requiring full eye examination or eye refraction.

In certain other inventive embodiments, one's vision correction is corrected, by way of one's electro-active lenses, to 20/20. This is obtained in most cases by correcting one's conventional refractive error (myopia, hyperopia, astigmatism, and/or presbyopia). In certain other inventive embodiments, non-conventional refractive error such as aberrations, irregular astigmatism, and/or ocular layer irregularities of the eye are measured and corrected, as well as conventional refractive error (myopia, hyperopia, astigmatism and/or presbyopia). In the inventive embodiments whereby aberrations, irregular astigmatism, and/or ocular layer irregularities of the eye are corrected in addition to conventional refractive error, one's vision can be corrected in many cases to better than 20/20, such as to 20/15, to better than 20/15, to 20/10, and/or to better than 20/10.

This advantageous error correction is accomplished by utilizing the electro-active lenses in the eyewear effectively as an adaptive optic. Adaptive optics have been demonstrated and in use for many years to correct for atmospheric distortion in ground-based astronomical telescopes, as well as for laser transmission through the atmosphere for communications and military applications. In these cases, segmented or "rubber" mirrors are usually employed to make small corrections to the wave front of the image or laser lightwave. These mirrors are manipulated by mechanical actuators in most cases.

Adaptive optics, as applied to vision, is based on active probing of the ocular system with a light beam, such as an eye-safe laser, and measures the wavefront distortion of either the retinal reflection or the image created on the retina. This form of wavefront analysis assumes a plane or spherical probe wave and measures the distortion imparted on this wavefront by the ocular system. By comparing the initial wavefront with the distorted one, a skilled examiner can determine what abnormalities exist in the ocular system and prescribe an appropriate corrective prescription. There are several competing designs for wavefront analyzers, however, the adaption of the electro-active lenses described here for use as either a transmissive or reflective spatial light modulator to perform such wavefront analysis is included within the invention. Examples of wavefront analyzers are provided in U.S. Pat. No. 5,777,719 (Williams) and U.S. Pat. No. 5,949,521 (Williams), each of which is herein incorporated by reference in its entirety.

In certain embodiments of the present invention, however, small corrections or adjustments are made to the electro-active lenses so that an image lightwave is imparted by a grid array of electrically driven pixels whose index of refraction can be altered, accelerating or slowing down the light passing through them by the alterable index. In this way, the electro-active lens becomes an adaptive optic, which can compensate for the inherent spatial imperfection in the optics of the eye itself in order to obtain a nearly aberration-free image on the retina.

In certain inventive embodiments, because the electro-active lens is fully two-dimensional, fixed spatial aberrations caused by the eye's optical system can be compensated for by incorporating the small index of refraction corrections on top of the gross vision correction prescription needs of the patient/user. In this way, vision can be corrected to a level of better than what could be achieved with common convergence and accommodation corrections, and, in many cases, could result in vision better than 20/20.

In order to achieve this better than 20/20 correction, the patient's ocular aberrations can be measured by, for example, a modified auto refractor utilizing a wavefront sensor or analyzer designed specifically for eye aberration measurements. Once the ocular aberrations and other types of non-conventional refractive error have been determined in both magnitude and spatially, the controller in the eyewear can be programmed to incorporate the 2-D spatially-dependent index of refraction changes to compensate for these aberrations and other types of non-conventional refractive error in addition to the overall myopia, hyperopia, presbyopia, and/or astigmatism correction. Thus, embodiments of the electro-active lens of the present invention can electro-actively correct for aberrations of the patient's ocular system or created by the lens optic.

Thus, for example, a certain power correction of −3.50 diopters may be required in a certain electro-active divergent lens to correct a wearer's myopia. In this case, an array of different voltages, $V_1 \ldots V_N$, is applied to the M elements in the grid array to generate an array of different indices of refraction, $N_1 \ldots N_M$, which give the electro-active lens a power of −3.50 diopters. However, certain elements in the grid array may require up to plus or minus 0.50 units change in their index $N_1 \ldots N_M$ to correct for ocular aberrations and/or non-conventional refractive error. The small voltage deviations corresponding to these changes is applied to the appropriate grid element, in addition to the base myopia-correcting voltages.

Figure 6:
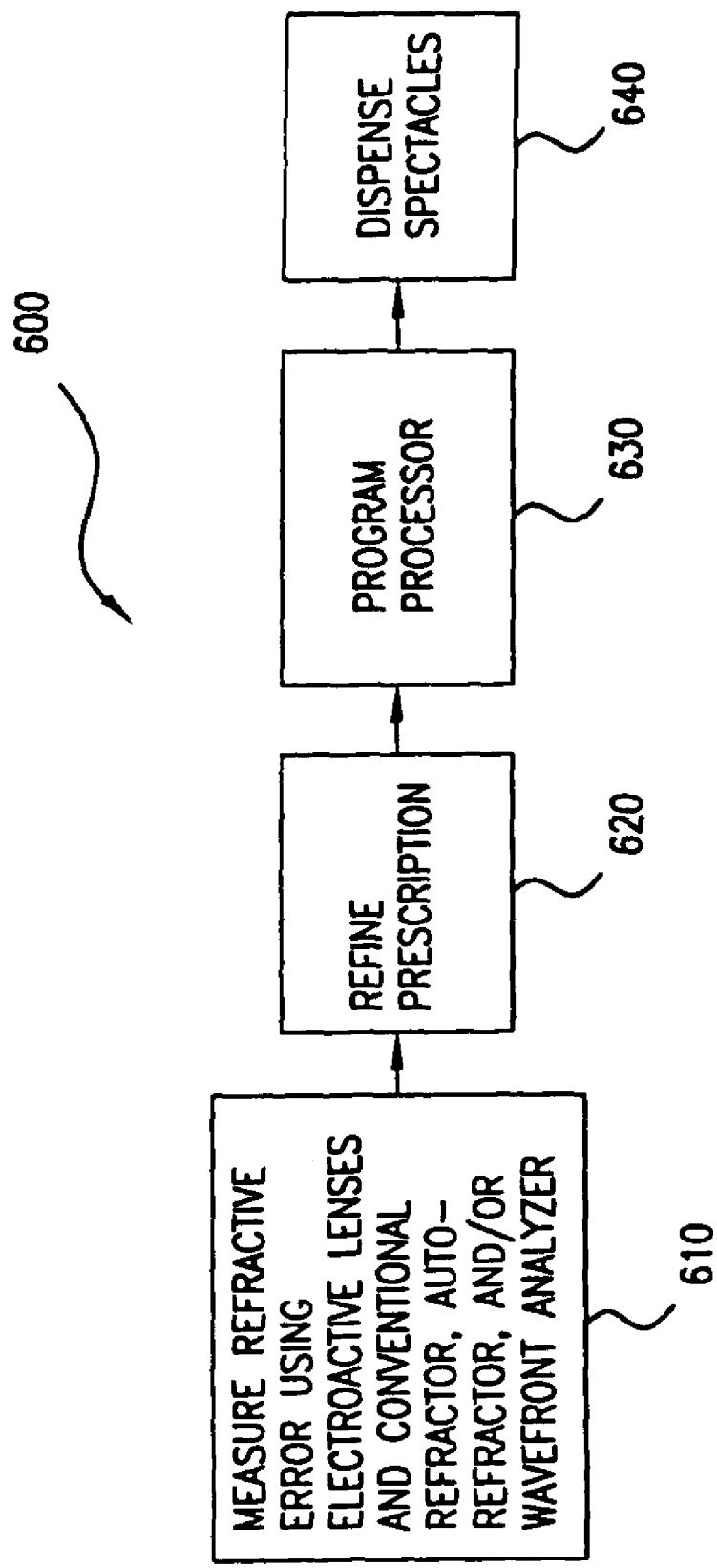
FIG. 6 is a flow diagram of an embodiment of prescription method 600.

In order to detect, quantify, and/or correct as much as possible for non-conventional refractive error such as irregular astigmatism, ocular refractive irregularities, such as for example, the tear layer on the front of the cornea, the front, or back of the cornea, aqueous irregularities, the front or back of the lenticular lens, vitreous irregularities, or for other aberrations caused by the ocular refractive system itself, the electro-active refractor/phoropter is used according to an embodiment of the inventive prescription method 600 of FIG. 6.

At step 610, either a conventional refractor, an electro-active refractor having both conventional and electro-active lenses, or an electro-active refractor having only electro-active lenses, or an auto-refractor, is utilized to measure one's refractive error using conventional lens powers such as minus power (for myopes), plus power (for hyperopes), cylindrical power and axis (for astigmatism) and prism power when needed. Utilizing this approach, one will get what is known today as the patient's BVA (best visual acuity) by way of conventional corrective refractive error. However, certain embodiments of the invention allow for improving one's vision beyond what today's conventional refractor/phoropters will achieve.

Therefore, step 610 provides for further refinement of one's prescription in a non-conventional inventive way. In step 610, the prescription, which accomplishes this end point, is programmed into the electro-active refractor. The patient is properly positioned to look through the electro-active lenses having a multi-grid electro-active structure into a modified and compatible autorefractor or a wavefront analyzer, which automatically measures precisely the refractive error. This refractive error measurement detects and quantifies as much non-conventional refractive errors as possible. This measurement is taken through a small, approximately 4.29 mm, targeted area of each electro-active lens, while automatically computing the necessary prescription to achieve the best focus on the fovea along the line-of-sight while the patient is looking through the targeted area of the electro-active lens. Once this measurement is made this non-conventional correction is either stored in the controller/programmer memory for future use or it is then programmed into the controller that controls the electro-active lenses. This, of course, is repeated for both eyes.

At step 620, the patient or wearer now may at their option elect to use a control unit which will allow them to further refine the conventional refractive error correction, the non-conventional refractive error correction, or a combination of both, and thus the final prescription, to their liking. Alternatively, or in addition, the eyecare professional may refine it, until in some cases no further refinement is performed. At this point, an improved BVA for the patient, better than any available via conventional techniques, will be achieved.

At step 630, any further refined prescription is then programmed into the controller, which controls the electro-active lenses' prescription. At step 640, the programmed electro-active spectacles are dispensed.

While the preceding steps 610 through 640 present an embodiment of one inventive method, depending upon the eyecare professional's judgement or approach, numerous different but similar approaches could be used to detect, quantify, and/or correct one's vision using solely electro-active refractors/phoropters or in combination with wavefront analyzers. Any method, no matter in what sequence, that utilizes an electro-active refractor/phoropter to detect, quantify, and/or correct one's vision, whether in conjunction with a wavefront analyzer or not, is considered part of the invention. For example, in certain inventive embodiments, steps 610 through 640 may be performed in either a modified way or even a different sequence. Furthermore, in embodiments of certain other inventive methods, the targeted area of the lens referred to in step 610 is within the range of about 3.0 millimeters in diameter to about 8.0 millimeters in diameter. Still in other inventive embodiments, the targeted area can be anywhere from about 2.0 millimeters in diameter up to the area of the entire lens.

Although this discussion has thus far concentrated on refraction using various forms of electro-active lenses alone or in combination with wavefront analyzers to perform the eye examination of the future, there is another possibility that new emerging technology may allow simply for objective measurements, thus potentially eliminating the need for a patient's communicated response or interaction. Many of the inventive embodiments described and/or claimed herein are intended to work with any type of measuring system, whether objective, subjective, or a combination of both.

Turning now to the electro-active lens itself, as discussed above, an embodiment of the present invention concerns an electro-active refractor/phoropter that has a novel electro-active lens, that can either be of a hybrid or of a non-hybrid construction. By hybrid construction it is meant a combination of a conventional single vision or a multifocal lens optic, with at least one electro-active zone located on the front surface, back surface, and/or in between the front and back surfaces, the zone consisting of an electro-active material having the necessary electro-active means to change focus electrically. In certain embodiments of the invention, the electro-active zone is specifically placed either inside the lens or on the back concave surface of the lens to protect it from scratches and other normal wear. In the embodiment where the electro-active zone is included as part of the front convex surface, in most cases a scratch resistant coating is applied. The combination of the conventional single vision lens or a conventional multifocal lens and the electro-active zone gives the total lens power of the hybrid lens design. By non-hybrid it is meant a lens which is electro-active whereby mostly 100% of its refractive power is generated solely by its electro-active nature.

Figure 7:
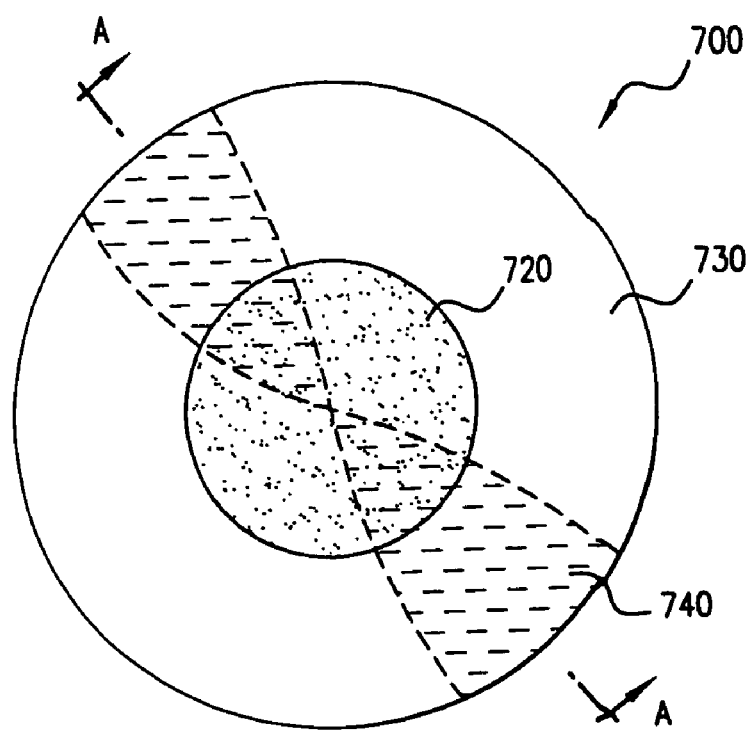
FIG. 7 is a front view of an embodiment of a hybrid electro-active spectacle lens 700.
Figure 8:
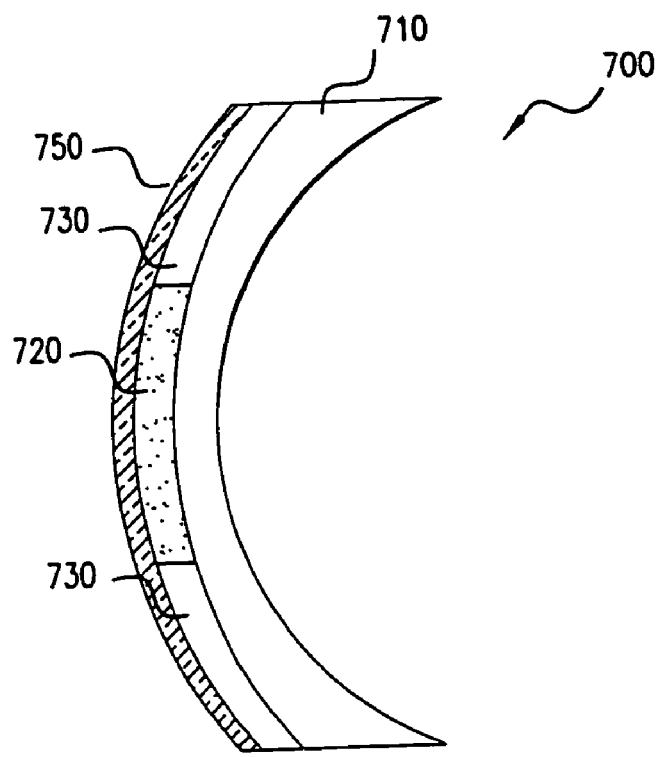
FIG. 8 is a section view of an embodiment of hybrid electro-active spectacle lens 700 taken along section line A—A of FIG. 7.

FIG. 7 is a front view, and FIG. 8 is a section view taken along line A—A, of an embodiment of an exemplary hybrid electro-active spectacle lens 700. In this illustrative example, lens 700 includes a lens optic 710. Attached to lens optic 710 is an electro-active layer 720, that can have one or more electro-active regions that occupy all or a portion of electro-active layer 720. Also attached to lens optic 710 and at least partially surrounding electro-active layer 720 is framing layer 730. Lens optic 710 includes an astigmatic power correction region 740 having an astigmatic axis A—A rotated, in this specific example only, approximately 45 degrees clockwise from horizontal. Covering electro-active layer 720 and framing layer 730 is an optional cover layer 750.

As will be discussed further, electro-active layer 720 can include a liquid crystal and/or a polymer gel. Electro-active layer 720 can also include an alignment layer, a metallic layer, a conducting layer, and/or an insulating layer.

In an alternative embodiment, astigmatic correction region 740 is eliminated so that lens optic 710 corrects for sphere power only. In another alternative embodiment, lens optic 710 can correct for either far distance, near distance, and/or both, and any sort of conventional refractive error, including spheric, cylindric, prismatic, and/or aspheric errors. Electro-active layer 720 can also correct for near distance, and/or for non-conventional refractive error such as aberrations. In other embodiments, electro-active layer 720 can correct any sort of conventional or non-conventional refractive error and lens optic 710 can correct for conventional refractive error.

It has been discovered that an electro-active lens having a hybrid construction approach has certain distinct advantages over that of a non-hybrid lens. These advantages are lower electrical power needs, smaller battery size, longer battery life expectancy, less complex electrical circuitry, fewer conductors, fewer insulators, lower manufacturing costs, increased optical transparency, and increased structural integrity. However, it must be noted that non-hybrid electro-active lenses have their own set of advantages, including reduced thickness and mass manufacturing.

It also has been discovered that both the non-hybrid, and in some embodiments, the full field hybrid and partial field hybrid approach, will allow for mass manufacturing of a very limited number of SKUs (Stock Keeping Units) when, for example, the electro-active structural design utilized is that of a multi-grid electro-active structure. In this case, it would only be necessary when mass manufacturing to focus primarily on a limited number of differentiated features such as curvature and size for the wearer's anatomical compatibility.

To understand the significance of this improvement, one must understand the number of traditional lens blanks needed to address most prescriptions. About 95% of corrective prescriptions include a sphere power correction within a range of −6.00 diopters to +6.00 diopters, in 0.25 diopter increments. Based on this range, there are about 49 commonly prescribed sphere powers. Of those prescriptions that include an astigmatism correction, about 95% fall within the range of −4.00 diopters to +4.00 diopters, in 0.25 diopter increments. Based on this range, there are about 33 commonly prescribed astigmatic (or cylinder) powers. Because astigmatism has an axis component, however, there are about 360 degrees of astigmatic axis orientations, which are typically prescribed in 1 degree increments. Thus, there are 360 different astigmatic axis prescriptions.

Moreover, many prescriptions include a bifocal component to correct for presbyopia. Of those prescriptions that have a presbyopic correction, about 95% fall within the range of +1.00 to +3.00 diopters, in 0.25 diopter increments, thereby resulting in about 9 commonly prescribed presbyopic powers.

Because some embodiments of the invention can provide for spherical, cylindrical, axis, and presbyopic corrections, one non-hybrid electro-active lens can serve the 5,239,080 (=49×33×360×9) different prescriptions. Thus, one non-hybrid electro-active lens can eliminate the need to mass manufacture and/or stock numerous lens blank SKUs, and of possibly greater importance, can eliminate the need to grind and polish each lens blank to a particular patient's prescription.

To account for the various lens curvatures that may be needed to accommodate anatomical issues such as face shape, eyelash length, etc., somewhat more than one non-hybrid electro-active lens SKU could be mass manufactured and/or stocked. Nevertheless, the number of SKU's could be reduced from millions to about five or less.

In the case of the hybrid electro-active lens, it has been discovered that by correcting for conventional refractive error with the lens optic and utilizing a mostly centered electro-active layer, it is possible to also reduce the number of SKU's needed. Referring to FIG. 7, lens 700 can be rotated as needed to place astigmatic axis A—A in the needed position. Thus, the number of hybrid lens blanks needed can be reduced by a factor of 360. Moreover, the electro-active zone of the hybrid lens can provide the presbyopic correction, thereby reducing by a factor of 9 the number of lens blanks needed. Thus, a hybrid electro-active lens embodiment can reduce from more than 5 million to 1619 (=49×33) the number of lens blanks needed. Because it may be reasonably possible to mass manufacture and/or stock this number of hybrid lens blank SKUs, the need for grinding and polishing may be eliminated.

Figure 28:
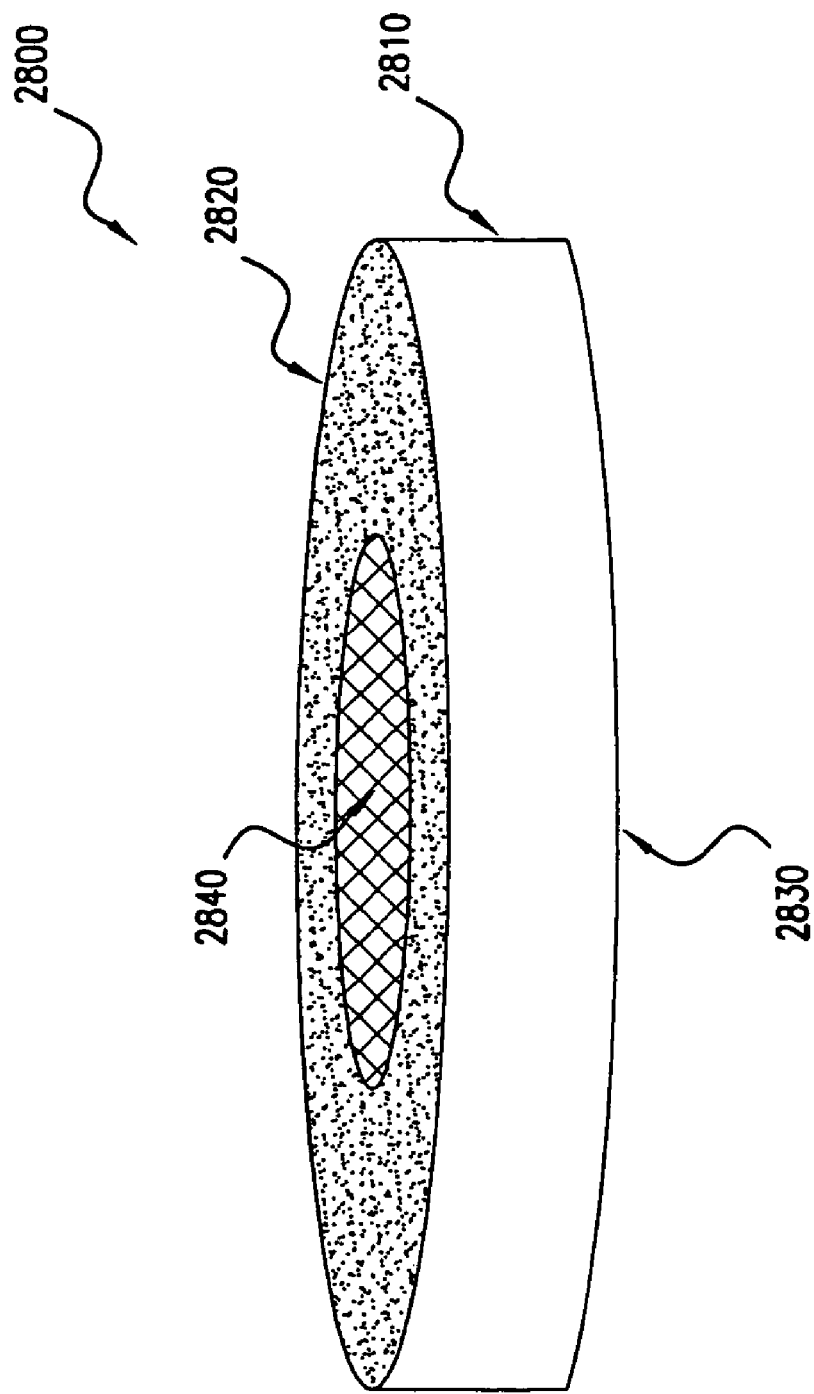
FIG. 28 is a perspective view of an embodiment of an electro-active lens 2800.

Nevertheless, grinding and polishing semi-finished hybrid lens blanks into finished lens blanks remains a possibility. FIG. 28 is a perspective view of an embodiment of a semi-finished lens blank 2800. In this embodiment, semi-finished lens blank 2800 has a lens optic 2810 with a finished surface 2820, an unfinished surface 2830, and a partial field electro-active layer 2840. In another embodiment, semi-finished lens blank 2800 can have a full field electro-active layer. Moreover, the electro-active structure of semi-finished lens blank 2800 can be multi-grid or single interconnect. Further, semi-finished lens blank 2800 can have refractive and/or diffractive characteristics.

In either the hybrid or the non-hybrid embodiment of the electro-active lens, a significant number of needed correcting prescriptions can be created and customized by the electro-active lens which can be adjusted and controlled by a controller that has been customized and/or programmed for the patient's specific prescription needs. Thus, the millions of prescriptions and numerous lens styles, single vision lens blanks, as well as the numerous multifocal semi-finished lens blanks may be no longer needed. In fact, most lens and frame manufacturing and distribution, as we know it may be revolutionized.

It should be noted that the invention includes both non-hybrid electro-active lenses, as well as full and partial field specific hybrid electro-active lenses that are either pre-manufactured electronic eyewear (frame and/or lenses) or customized electronic eyewear at the time of delivery to the patient or customer. In the case of the eyewear being pre-fabricated and assembled, both the frames and the lenses are pre-made with the lenses already edged and put into the eyeglass frames. Also considered to be part of the invention is the programmable and re-programmable controller as well as the mass production of frames and lenses having the necessary electric components which can be prefabricated and sent to the eyecare professional's site or some other site for either the installation of, for example, a programmed controller, and/or one or more controller components, for the patient's prescription.

In certain cases the controller, and/or one or more controller components, can be part of the pre-manufactured frame and electro-active lens assembly and then programmed at either the eyecare professional's site or some other site. The controller, and/or one or more controller components, can be in the form, for example, of a chip or a thin film and can be housed in the frame, on the frame, in the lens, or on the lens of the eyeglasses. The controller, and/or one or more controller components, can be re-programmable or not re-programmable based upon the business strategy to be implemented. In the case where the controller, and/or one or more controller components, is re-programmable, this will allow for the repeated updating of one's prescriptions as long as the patient or customer is happy with his or her eyeglass frames as well as the cosmetic appearance and functionality of the electro-active lenses.

In the case of the latter, the non-hybrid and hybrid electro-active lens embodiments just discussed, the lenses must be structurally sound enough in order to protect the eye from injury from a foreign object. In the United States, most eyewear lenses must pass a FDA required impact test. In order to meet these requirements, it is important that a support structure is built into or on the lens. In the case of the hybrid type, this is accomplished, for example, utilizing either a prescription or non-prescription single vision or multifocal lens optic as a structural base. For example, the structural base for the hybrid type can be made out of polycarbonate. In the case of the non-hybrid lens, in certain embodiments, the electro-active material selected and thickness accounts for this needed structure. In other embodiments, the non-prescription carrier base or substrate onto which the electro-active material is positioned accounts for this needed protection.

When utilizing electro-active zones in spectacle lenses in certain hybrid designs, it can be essential to maintain proper distance correction when a power interruption to the lenses occurs. In the case of a battery or wiring failure, in some situations it could be disastrous if the wearer was driving an automobile or piloting an airplane and their distance correction was lost. To prevent such occurrences, the inventive design of the electro-active spectacle lenses can provide for the distance correction to be maintained when the electro-active zones is in the OFF position (the inactivated or unpowered state). In an embodiment of this invention, this can be accomplished by providing the distance correction with a conventional fixed focal length optic, whether it be a refractive or a diffractive hybrid type. Any additional add power, therefore, is provided by the electro-active zone(s). Thus, a fail-safe electro-active system occurs, because the conventional lens optic will preserve the wearer's distance correction.

Figure 9:
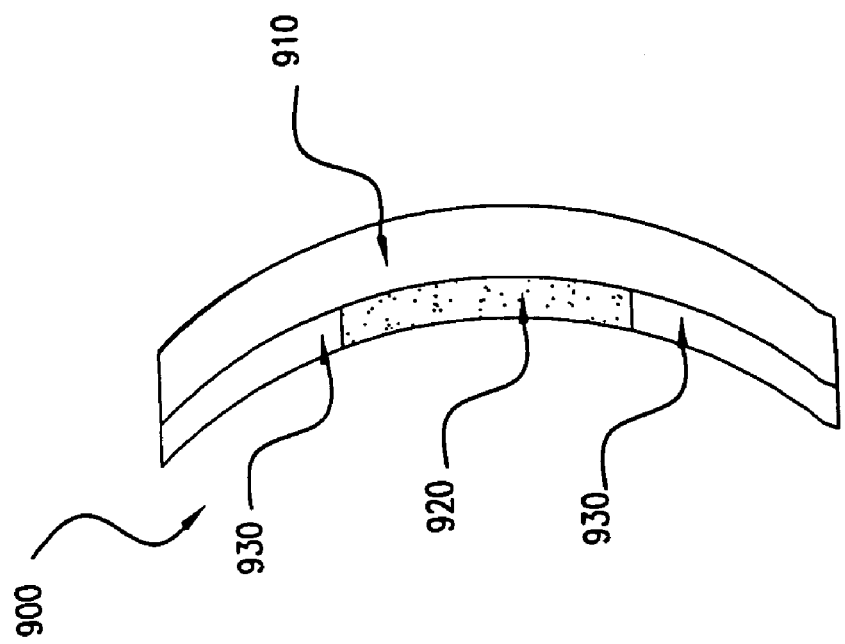
FIG. 9 is a section view of an embodiment of an electro-active lens 900, taken along section line Z—Z of FIG. 5.

FIG. 9 is a side view of an exemplary embodiment of another electro-active lens 900 having a lens optic 910 that is index matched to an electro-active layer 920. In this illustrative example, the diverging lens optic 910, having an index of refraction, $n_1$, provides distance correction. Attached to lens optic 910 is the electro-active layer 920, which can have an unactivated state, and a number of activated states. When electro-active layer 920 is in its unactivated state, it has an index of refraction $n_2$, which approximately matches the index of refraction, $n_1$, of lens optic 910. More accurately, when unactivated, $n_2$ is within 0.05 refractive units of $n_1$. Surrounding electro-active layer 920 is framing layer 930, which has an index of refraction, $n_3$, that also approximately matches the index of refraction, $n_1$, of lens optic 910 within 0.05 refractive units of $n_1$.

Figure 10:
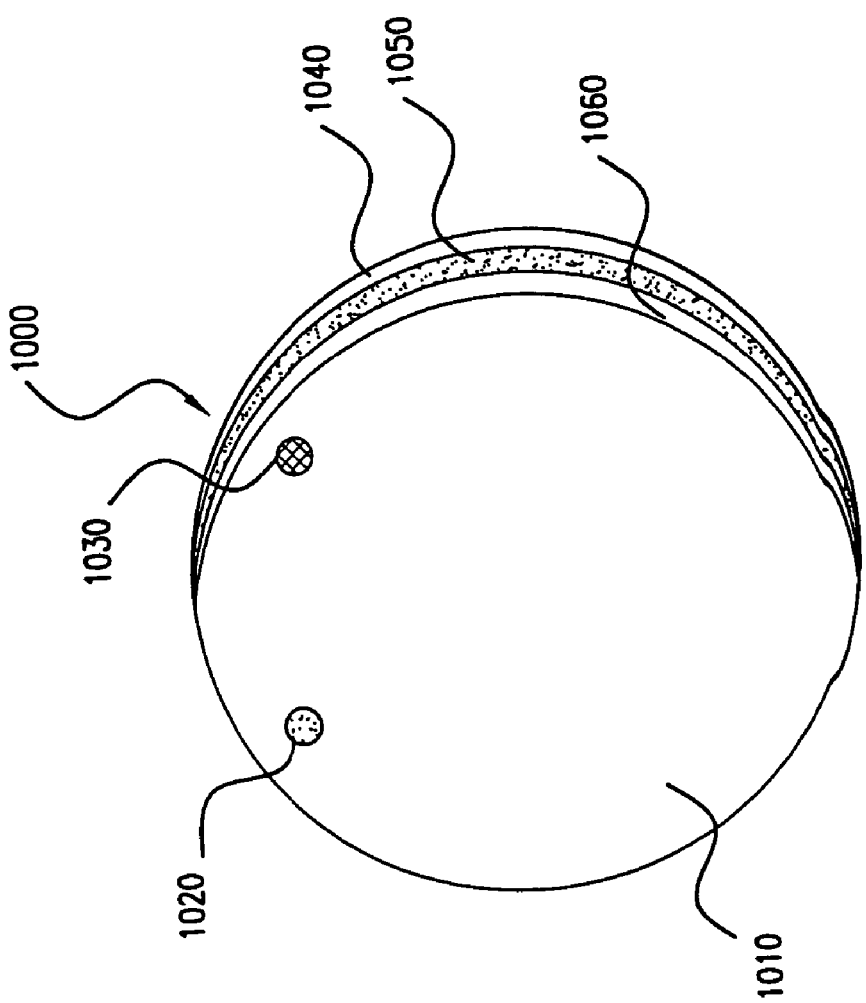
FIG. 10 is a perspective view of an embodiment of an electro-active lens system 1000.

FIG. 10 is a perspective view of an exemplary embodiment of another electro-active lens system 1000. In this illustrative example, electro-active lens 1010 includes a lens optic 1040 and an electro-active layer 1050. A rangefinder transmitter 1020 is positioned on electro-active layer 1050. Also, a rangefinder detector/receiver 1030 is positioned on electro-active layer 1050. In an alternative embodiment, either transmitter 1020 or receiver 1030 can be positioned in electro-active layer 1050. In other alternative embodiments, either transmitter 1020 or receiver 1030 can be positioned in or on lens optic 1040. In other embodiments either transmitter 1020 or receive 1030 can be positioned on outer covering layer 1060. Further, in other embodiments, 1020 and 1030 can be positioned on any combination of the preceding.

Figure 11:
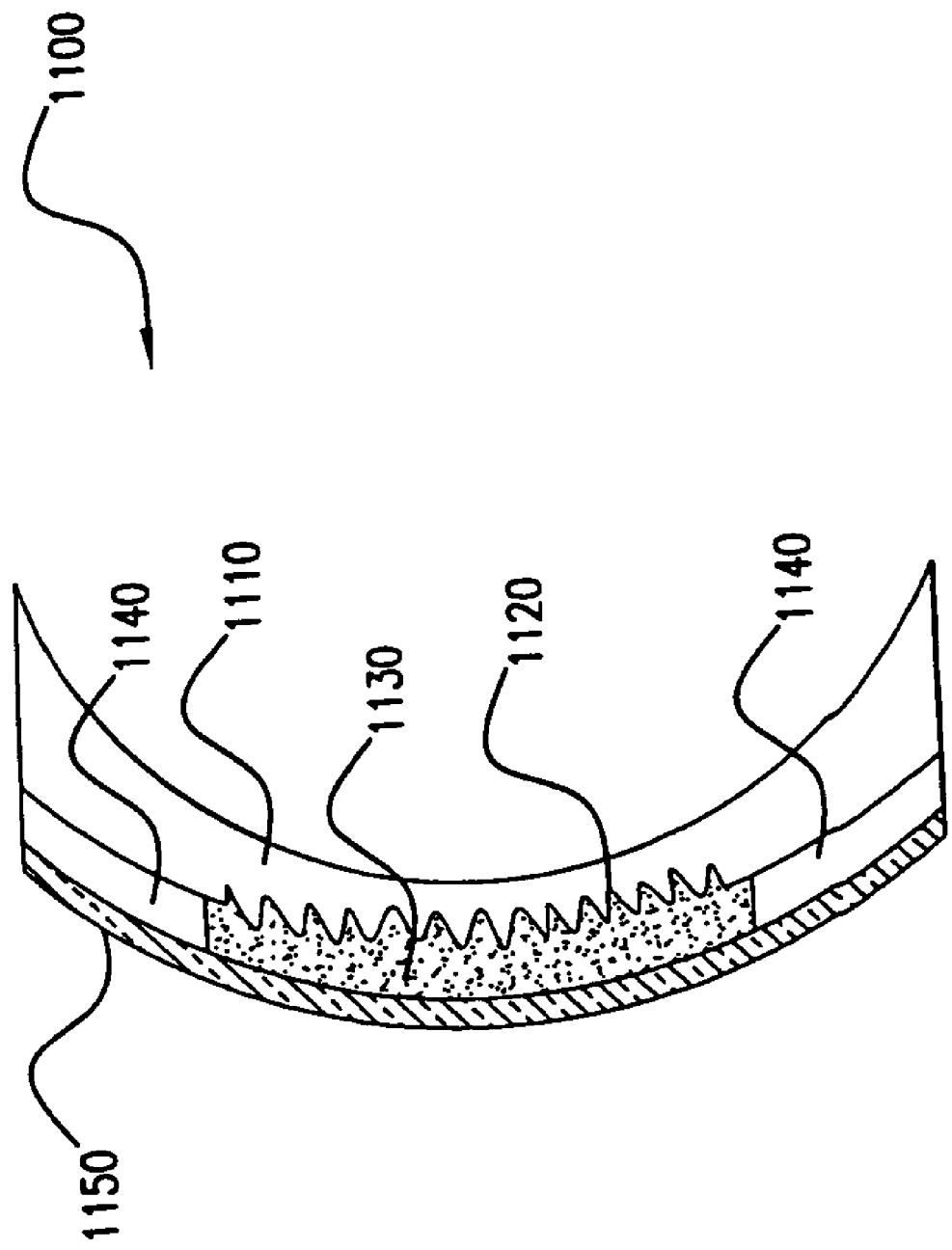
FIG. 11 is a section view of an embodiment of a diffractive electro-active lens 1100 taken along section line Z—Z of FIG. 5.

FIG. 11 is a side view of an exemplary embodiment of a diffractive electro-active lens 1100. In this illustrative example, lens optic 1110 provides distance correction. Etched on one surface of lens optic 1110 is diffractive pattern 1120, having an index of refraction, $n_1$. Attached to lens optic 1110 and covering diffractive pattern 1120 is electro-active layer 1130, which has an index of refraction, $n_2$, that approximates $n_1$, when electro-active layer 1130 is in its unactivated state. Also attached to lens optic 1110 is framing layer 1140, which is constructed of material mostly identical to lens optic 1110, and which at least partially surrounds electro-active layer 1120. A covering 1150 is attached over electro-active layer 1130 and framing layer 1140. The framing layer 1140 can also be an extension of lens optic 1110, in which can no actual layer is added, however, lens optic 1110 is fabricated so as to frame or circumscribe electro-active layer 1130.

Figure 13:
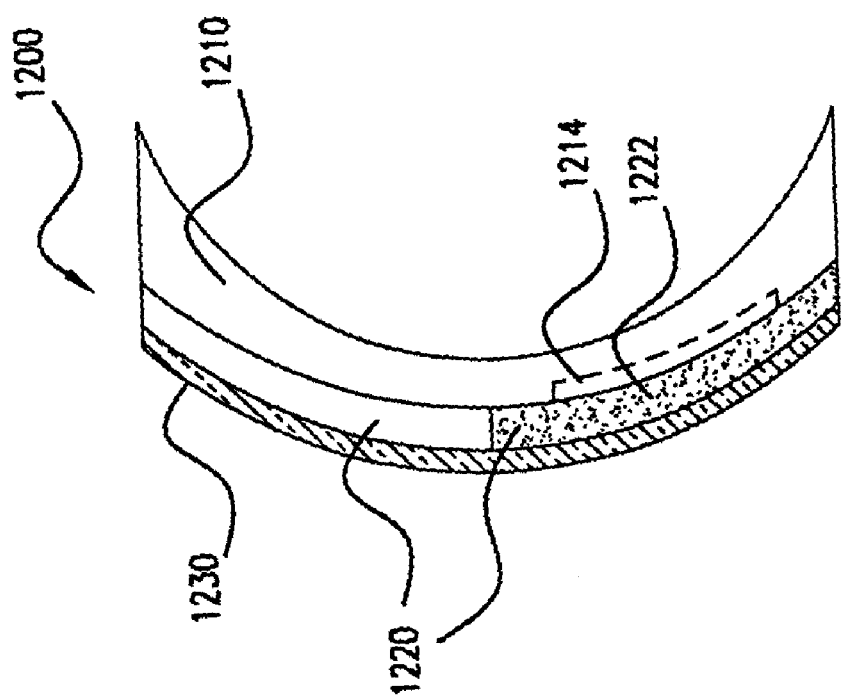
FIG. 13 is a section view of an embodiment of the electro-active lens 1200 of FIG. 12 taken along section line Q—Q.
Figure 12:
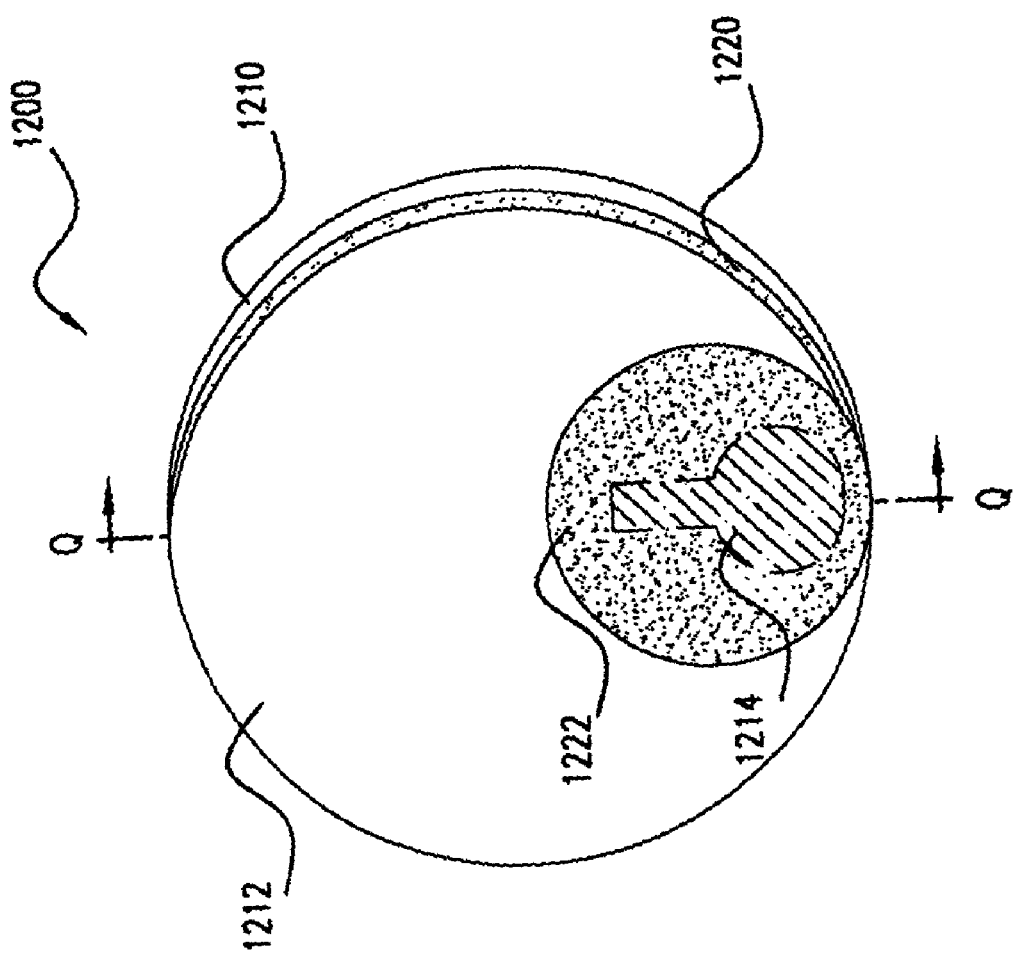
FIG. 12 is a front view of an embodiment of an electro-active lens 1200.

FIG. 12 is a front view, and FIG. 13 a side view, of an exemplary embodiment of an electro-active lens 1200 having a multi-focal optic 1210 attached to an electro-active framing layer 1220. In this illustrative example, multi-focal optic 1210 is of a progressive addition lens design. Moreover, in this illustrative example, multi-focal optic 1210 includes a first optical refraction focus zone 1212 and a second progressive addition optical refraction focus zone 1214. Attached to multi-focal optic 1210 is electro-active framing layer 1220 having an electro-active region 1222 that is positioned over second optical refraction focus zone 1214. A cover layer 1230 is attached to electro-active framing layer 1220. It should be noted that the framing layer can be either electro-active or non-electro-active. When the framing layer is electro-active, insulating material is utilized to insulate the activated region from the non-activated region.

In most inventive cases, but not all, in order to program the electro-active eyewear to correct one's vision to its optimum, thus, correcting for non-conventional refractive error it is necessary to track the line-of-sight of each eye by way of tracking the eye movements of the patient or wearer.

Figure 14:
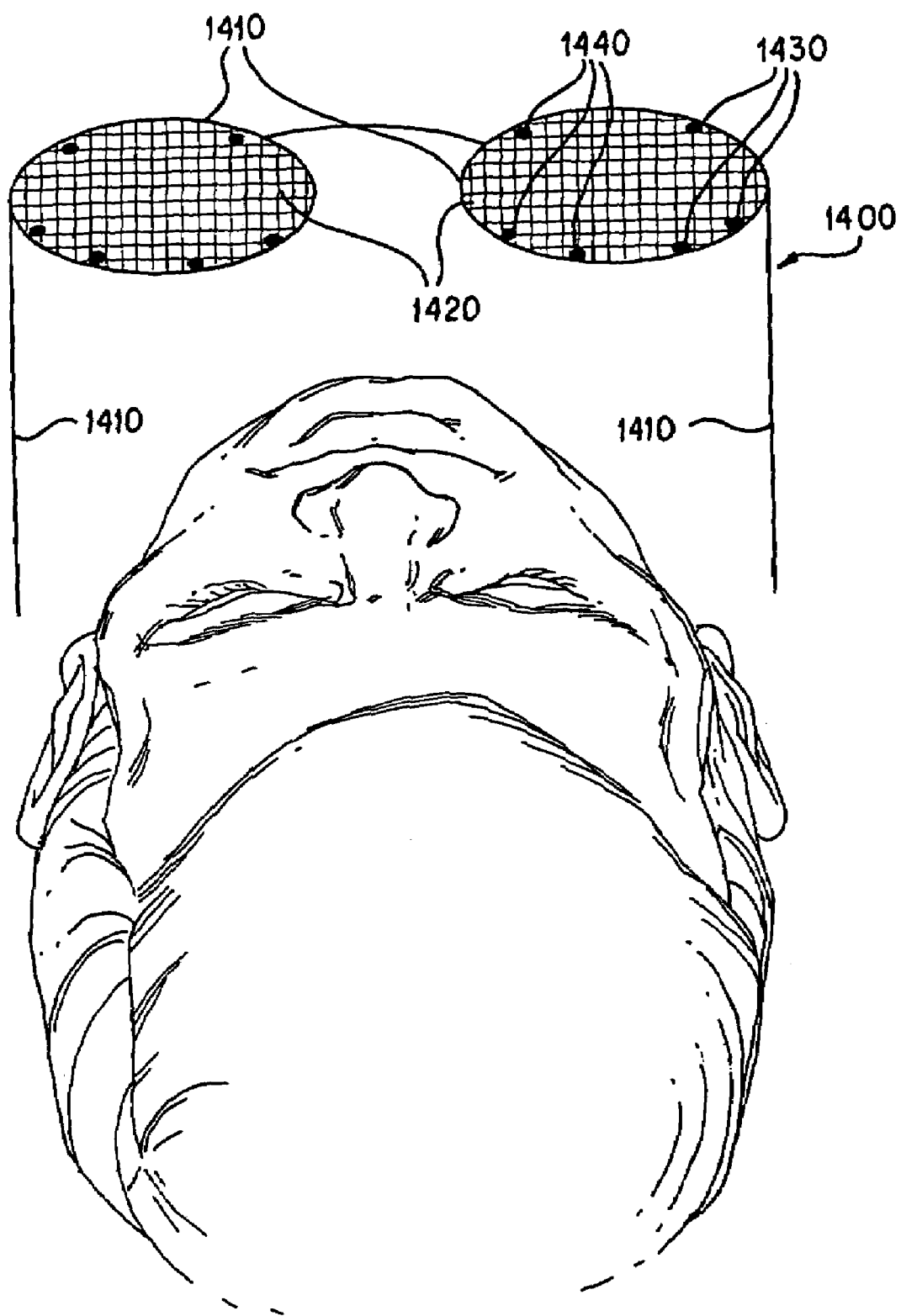
FIG. 14 is a perspective view of an embodiment of a tracking system 1400.

FIG. 14 is a perspective view of an exemplary embodiment of a tracking system 1400. Frames 1410 contain electro-active lens 1420. Attached to the backside of electro-active lens 1420 (that side closest to the wearer's eyes, also referred to as the proximal side), are a tracking signal sources 1430, such as light emitting diodes. Also attached to the backside of electro-active lens 1420 are tracking signal receivers 1440, such as light reflection sensors. Receivers 1440, and possibly sources 1430, are connected to a controller (not shown) that includes in its memory instructions to enable tracking. Utilizing this approach it is possible to locate very precisely the eye movements up, down, right, left and any variation thereof. This is needed as certain types, but not all, of non-conventional refractive error needs to be corrected and isolated within one's line-of-sight (for example, in the case of a specific corneal irregularity or bump that moves as the eye moves).

In various alternative embodiments, sources 1430 and/or receivers 1440 can be attached to the backside of frames 1410, embedded in the backside of frames 1410, and/or embedded in the backside of lenses 1420.

An important portion of any spectacle lens, including the electro-active spectacle lens, is the portion used to produce the sharpest image quality within the user's field of view. While a healthy person can see approximately 90 degrees to either side, the sharpest visual acuity is located within a smaller field of view, corresponding to the portion of the retina with the best visual acuity. This region of the retina is known as the fovea, and is approximately a circular region measuring 0.40 mm in diameter on the retina. Additionally, the eye images the scene through the entire pupil diameter, so the pupil diameter will also affect the size of the most critical portion of the spectacle lens. The resulting critical region of the spectacle lens is simply the sum of the diameter of the eye's pupil diameter added to the projection of the fovea's field of view onto the spectacle lens.

The typical range for the eye's pupil diameter is from 3.0 to 5.5 mm, with a most common value of 4.0 mm. The average fovea diameter is approximately 0.4 mm.

The typical range for the size of the fovea's projected dimension onto the spectacle lens is affected by such parameters as the length of the eye, the distance from the eye to the spectacle lens, etc.

The tracking system of this specific inventive embodiment then locates the regions of the electro-active lens that correlate to the eye movements relative to the fovial region of the patient's retina. This is important as the invention's software is programmed to always correct for the non-conventional refractive error that is correctable as the eye moves. Thus, it is necessary in most, but not all, inventive embodiments that correct for non-conventional refractive error to electro-actively alter the area of the lens that the line-of-sight is passing through as the eyes fixate their target or gaze. In other words, in this specific inventive embodiment the vast majority of the electro-active lens corrects for conventional refractive error and as the eye moves the targeted electro-active area focus moves as well by way of the tracking system and software to correct for the non-conventional refractive error taking into account the angle in which the line-of-sight intersects different sections of the lens and factoring this into the final prescription for that specific area.

In most, but not all, inventive embodiments, the tracking system and enabling software is utilized to correct one's vision to its maximum, while looking or gazing at distant objects. When looking at near points the tracking system, if used, is utilized to both calculate the range of near point focus in order to correct for one's accommodative and convergence near or intermediate range focusing needs. This of course is programmed into the electro-active eyewear controller, and/or one or more controller components, as part of the patient or wearers' prescription. In still other inventive embodiments a range finder and/or tracking system is incorporated either into the lenses and/or frames.

It should be pointed out that in other inventive embodiments such as those that correct for certain types of non-conventional refractive error, such as, for example, irregular astigmatism, in most but not all cases, the electro-active lenses do not need to track the patient or wearer's eye. In this case the overall electro-active lens is programmed to correct for this, as well as the other conventional refractive error of the patient.

Also, since aberrations are directly related to the viewing distance, it has been discovered that they can be corrected in relation to the viewing distance. That is, once the aberration or aberrations have been measured, it is possible to correct for these aberrations in the electro-active layer by way of segregating the electro-active regions so as to electro-actively correct for aberrations for specific distances such as distance vision, intermediate vision, and/or near vision. For example, the electro-active lens can be segregated into a far vision, intermediate vision, and near vision corrective zones, each the software controlling each zone causing the zone to correct for those aberrations that impact the corresponding viewing distance. Therefore in this specific inventive embodiment, where the electro-active layer is segregated for different distances whereby each segregated region corrects for specific aberrations of a specific distance, it is possible to correct for non-refractive error without a tracking mechanism.

Finally, it should be pointed out that in another inventive embodiment, it is possible to accomplish the correction of the non-conventional refractive error, such as that caused by aberrations, without physically separating the electro-active regions and without tracking. In this embodiment, using the viewing distance as an input, the software adjusts the focus of a given electro-active area to account for the correction needed for an aberration that would otherwise impact the vision at the given viewing distance.

Furthermore, it has been discovered that either a hybrid or non-hybrid electro-active lens can be designed to have a full field or a partial field effect. By full field effect it is meant that the electro-active layer or layers cover the vast majority of the lens region within an eyeglass frame. In the case of a full field, the entire electro-active area can be adjusted to the desired power. Also, a full field electro-active lens can be adjusted to provide a partial field. However, a partial field electro-active specific lens design can not be adjusted to a full field due to the circuitry needed to make it partial field specific. In the case of a full field lens adjusted to become a partial field lens, a partial section of the electro-active lens can be adjusted to the desired power.

Figure 15:
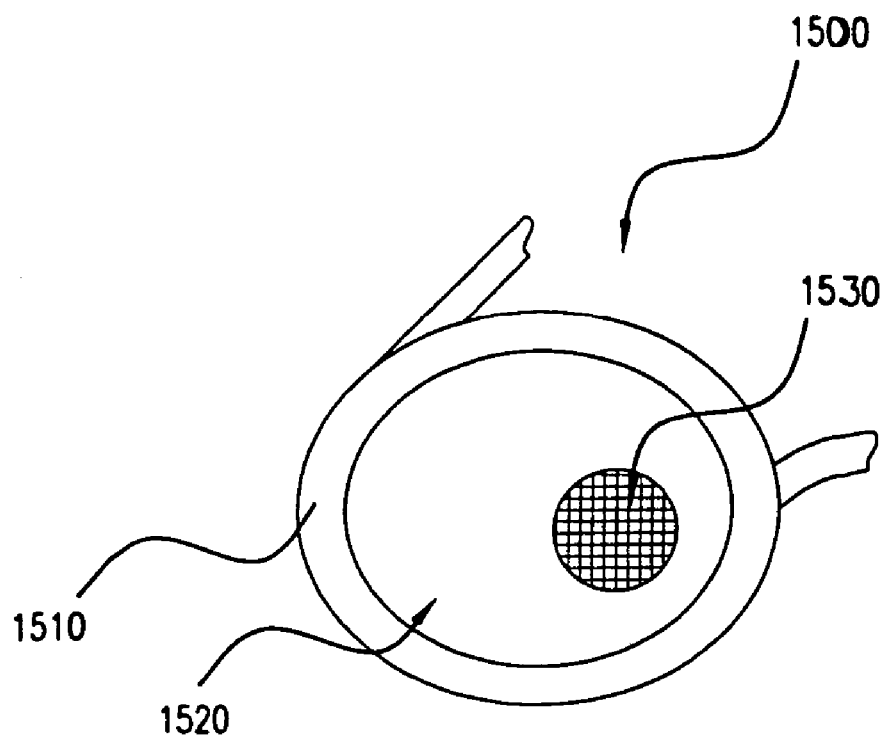
FIG. 15 is a perspective view of an embodiment of an electro-active lens system 1500.

FIG. 15 is a perspective view of an exemplary embodiment of another electro-active lens system 1500. Frames 1510 contain electro-active lenses 1520, which have a partial field 1530.

Figure 16:
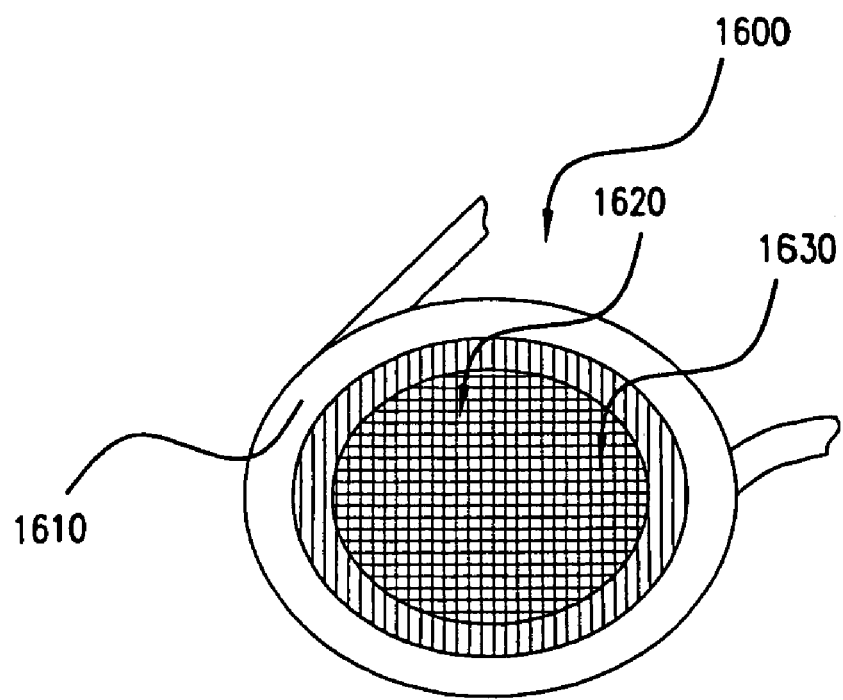
FIG. 16 is a perspective view of an embodiment of an electro-active lens system 1600.

For purposes of comparison, FIG. 16 is a perspective view of an exemplary embodiment of yet another electro-active lens system 1600. In this illustrative example, frames 1610 contain electro-active lenses 1620, which have a full field 1630.

In certain inventive embodiments the multifocal electro-active optic is pre-manufactured and in some cases, due to the significantly reduced number of SKU's required, even inventoried at the dispensing location as a finished multifocal electro-active lens blank. This inventive embodiment allows for the dispensing site to simply fit and edge the inventoried multifocal electro-active lens blanks into the electronic enabling frames. While in most cases this invention could be of a partial field specific type electro-active lens, it should be understood this would work for full field electro-active lenses, as well.

In one hybrid embodiment of the invention, a conventional single vision lens optic being of aspheric design or non-aspheric design having a toric surface for correction of astigmatism and a spherical surface is utilized to provide the distance power needs. If astigmatic correction is needed the appropriate power single vision lens optic would be selected and rotated to the proper astigmatic axis location. Once this is done the single vision lens optic could be edged for the eye wire frame style and size. The electro-active layer could then be applied on the single vision lens optic or the electro-active layer can be applied prior to edging and the total lens unit can be edged later. It should be pointed out that, for edging whereby the electro-active layer is affixed to a lens optic, either a single vision or multifocal electro-active optic, prior to edging, an electro-active material such as a polymer gel may be advantageous over a liquid crystal material.

The electro-active layer can be applied to compatible lens optics by way of different technologies known in the art. Compatible lens optics are optics whose curves and surfaces will accept the electro-active layer properly from the stand point of bonding, aesthetics, and/or proper final lens power. For example, adhesives can be utilized applying the adhesive directly to the lens optic and then laying down the electro-active layer. Also, the electro-active layer can be manufactured so it is attached to a release film in which case it can be removed and reattached adhesively to the lens optic. Also, it can be attached to two-way film carrier of which the carrier itself is attached adhesively to the lens optic. Furthermore, it can be applied utilizing a Surface-Casting technique in which case the electro-active layer is created in-situ.

In previously mentioned hybrid embodiment, FIG. 12, a combination of a static and non-static approach is used to satisfy one's mid and near point vision needs, a multifocal progressive lens 1210 having the proper needed distance correction and having, for example, approximately +1.00 diopter of full near add power is utilized in lieu of the single vision lens optic. In utilizing this embodiment the electro-active layer 1220 can be placed on either side of the multifocal progressive lens optic, as well as buried inside the lens optic. This electro-active layer is utilized to provide for additional add power.

When utilizing a lower add power in the lens optic than required by the overall multifocal lens, the final add power is the total additive power of the low multifocal add and the additional required near power generated by way of the electro-active layer. For example only; if a multifocal progressive addition lens optic had an add power of +1.00 and the electro-active layer created a near power of +1.00 the total near power for the hybrid electro-active lens would be+2.00D. Utilizing this approach, it is possible to significantly reduce unwanted perceived distortions from multifocal lenses, specifically progressive addition lenses.

In certain hybrid electro-active embodiments whereby a multifocal progressive addition lens optic is utilized, the electro-active layer is utilized to subtract out unwanted astigmatism. This is accomplished by neutralizing or substantially reducing the unwanted astigmatism through an electro-actively created neutralizing power compensation solely in the areas of the lens where the unwanted astigmatism exists.

In certain inventive embodiments decentration of the partial field is needed. When applying a decentered partial field electro-active layer it is necessary to align the electro-active layer in such a way to accommodate the proper astigmatic axis location of the single vision lens optic so as to allow for correcting one's astigmatism, should it exist, as well as locating the electronic variable power field in the proper location for one's eyes. Also, it is necessary with the partial field design to align the partial field location to allow for proper decentration placement with regards to the patient's pupillary needs. It has been further discovered that unlike conventional lenses where the static bifocal, multifocal or progressive regions are always placed to always be below one's distance-viewing gaze, the use of an electro-active lens allows for certain manufacturing freedom not available to conventional multifocal lenses. Therefore, some embodiments of the invention, the electro-active region is located where one would typically find the distance, intermediate, and near vision regions of a conventional non-electro-active multi-focal lens. For example, the electro-active region can be placed above the 180 meridian of the lens optic, thereby allowing the multifocal near vision zone to be occasionally provided above the 180 meridian of the lens optic. Providing the near vision zone above the 180 meridian of the lens optic can be especially useful for those spectacle wearers working at close distances to an object directly in front or overhead of the wearer, such as working with a computer monitor, or nailing picture frames overhead.

In the case of a non-hybrid electro-active lens or both the hybrid full field lens and for example, a 35 mm diameter hybrid partial field lens, the electro-active layer, as stated before, can be applied directly to either the single vision lens optic, or pre-manufactured with a lens optic creating electro-active finished multifocal lens blanks, or the multifocal progressive lens optic, prior to edging the lens for the shape of the frame's lens mounting. This allows for pre-assembly of electro-active lens blanks, as well as being able to inventory stock finished, but not edged electro-active lens blanks, thus allowing for just in time eyeglass fabrication at any channel of distribution, including the doctor or optician's offices. This will allow all optical dispensaries to be able to offer fast service with minimal needs for expensive fabrication equipment. This benefits manufacturers, retailers, and their patients, the consumers.

Considering the size of the partial field, it has been shown, for example, in one inventive embodiment that the partial field specific region could be a 35 mm diameter centered or decentered round design. It should be pointed out that the diameter size can vary depending upon the needs. In certain inventive embodiments 22 mm, 28 mm, 30 mm, & 36 mm round diameters are utilized.

The size of the partial field can depend on the structure of the electro-active layer and/or the electro-active field. At least two such structures are contemplated as within the scope of the present invention, namely, a single-interconnect electro-active structure and a multi-grid electro-active structure.

Figure 17:
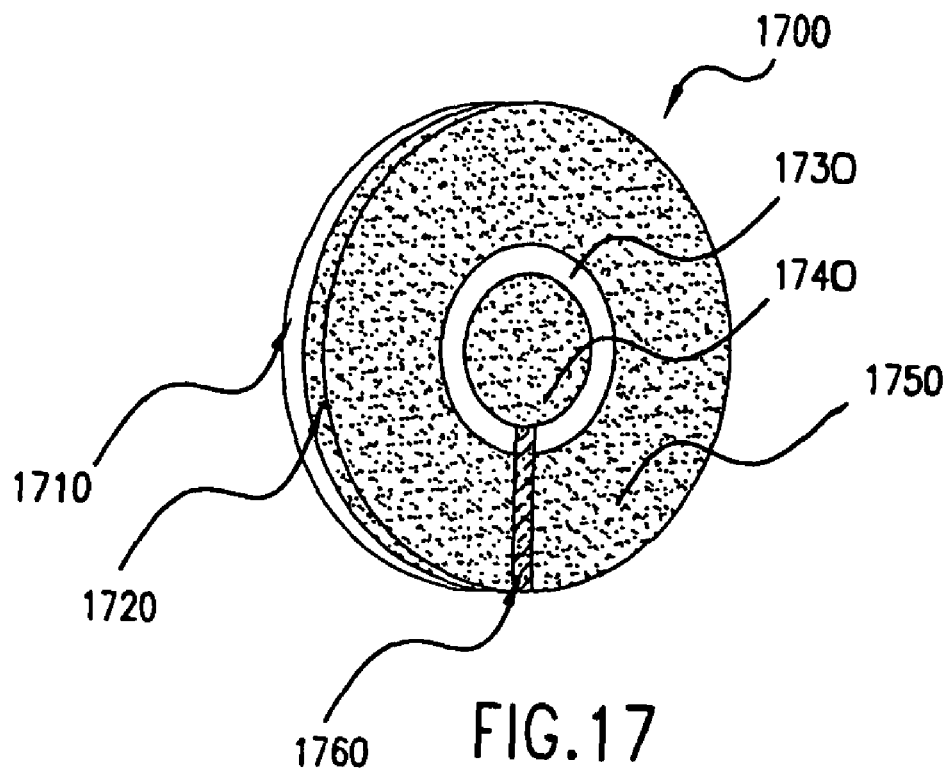
FIG. 17 is a perspective view of an embodiment of an electro-active lens 1700.

FIG. 17 is a perspective view of an embodiment of an electro-active lens 1700 having a single interconnect structure. Lens 1700 includes a lens optic 1710 and an electro-active layer 1720. Within electro-active layer 1720, an insulator 1730 separates an activated partial field 1740 from a framed non-activated field (or region) 1750. A single wire interconnect 1760 connects the activated field to a power supply and/or controller. Note that in most, if not all, embodiments, a single-interconnect structure has a single pair of electrical conductors coupling it to a power source.

Figure 18:
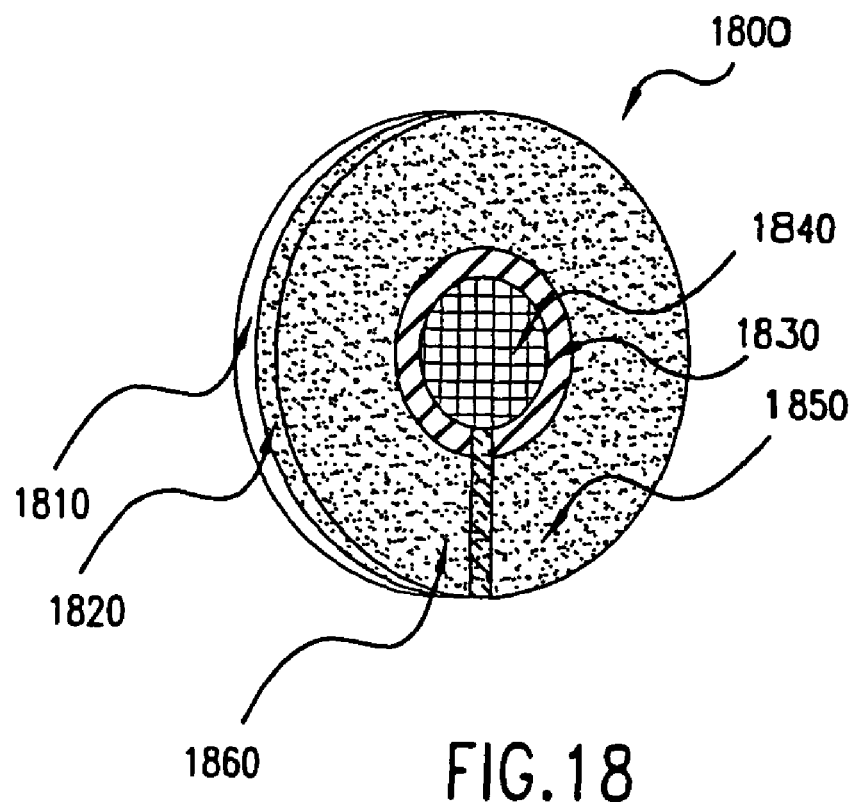
FIG. 18 is a perspective view of an embodiment of an electro-active lens 1800.

FIG. 18 is a perspective view of an embodiment of an electro-active lens 1800 having a multi-grid structure. Lens 1800 includes a lens optic 1810 and an electro-active layer 1820. Within electro-active layer 1820, an insulator 1830 separates an activated partial field 1840 from a framed non-activated field (or region) 1850. A plurality of wire interconnects 1860 connect the activated field to a power supply and/or controller.

When utilizing the smaller diameters for the partial field, it has been discovered that the electro-active thickness differential from edge to center of the partial field specific region when utilizing a single interconnect electro-active structure can be minimized. This has a very positive role in minimizing the electrical power needs, as well as number of electro-active layers required, especially for the single interconnect structure. This is not always the case for the partial field specific region whereby it utilizes a multi-grid electro-active structure. When utilizing a single interconnect electro-active structure, in many inventive embodiments, but not all, multiple single interconnect electro-active structures are layered within or on the lens so as to allow for multiple electro-active layers creating for example, a total combined electro-active power of +2.50D. In this inventive example only, five +0.50D single interconnect layers could be placed one on top of each other separated only in most cases, by insulating layers. In this way, the proper electrical power can create the necessary refractive index change for each layer by way of minimizing the electrical needs of one thick single interconnect layer which in some cases would be impractical to energize properly.

It should be further pointed out in the invention, certain embodiments having multiple single interconnect electro-active layers can be energized in a preprogrammed sequence to allow one to have the ability to focus over a range of distances. For example, two +0.50D single interconnect electro-active layers could be energized, creating a +1.00 intermediate focus to allow for a +2.00D presbyope to see at finger tip distance and then two additional +0.50D single interconnect electro-active layers could be energized to give the +2.00D presbyope the ability to read as close as 16 inches. It should be understood that the exact number of electro-active layers, as well as the power of each layer, can vary depending upon the optical design, as well as the total power needed to cover a specific range of near and intermediate vision distances for a specific presbyope.

Furthermore, in certain other inventive embodiments, a combination of either one or more single interconnect electro-active layers are present in the lens in combination with a multi-grid electro-active structural layer. Once again, this gives one the ability of focusing for a range of intermediate and near distances assuming the proper programming. Finally, in other inventive embodiments, only a multi-grid electro-active structure is utilized either in a hybrid or non-hybrid lens. Either way, the multi-grid electro-active structure in combination with a properly programmed electro-active eyewear controller, and/or one or more controller components, would allow for the ability to focus over a broad range of intermediate and near distances.

Also, semi-finished electro-active lens blanks that would allow for surfacing are also within the scope of the invention. In this case, either a decentered, centered, partial field electro-active layer incorporated with the blank, or a full field electro-active layer is incorporated with the blank and then surfaced to the correct prescription needed.

In certain embodiments the variable power electro-active field is located over the entire lens and adjusts as a constant spherical power change over the entire surface of the lens to accommodate one's working near vision focusing needs. In other embodiments the variable power field adjusts over the entire lens as a constant spherical power change while at the same time creating an aspherical peripheral power effect in order to reduce distortion and aberrations. In some of the embodiments mentioned above, the distance power is corrected by way of either the single vision, multifocal finished lens blanks, or the multifocal progressive lens optic. The electro-active optical layer corrects mainly for the working distance focusing needs. It should be noted this is not always the case. It is possible, in some cases, to utilize either a single vision, multifocal finished lens optic, or multifocal progressive lens optic for distance spherical power only and correct near vision working power and astigmatism through the electro-active layer or utilize either the single vision or multifocal lens optic to correct astigmatism only and correct the sphere power and near vision working power through the electro-active layer. Also, it is possible to utilize a plano, single vision, multifocal finished lens optic, or progressive multifocal lens optic and correct the distance sphere and astigmatism needs by way of the electro-active layer.

It should be pointed out that with the invention, the power correction needed, whether prismatic, spherical or aspheric power as well as total distance power needs, mid range power needs and near point power needs, can be accomplished by way of any number of additive power components. These include the utilization of a single vision or finished multifocal lens optic providing all the distance spherical power needs, some of the distance spherical power needs, all of the astigmatic power needs, some of the astigmatic power needs, all of the prismatic power needs, some of the prismatic power needs, or any combination of the above when combined with the electro-active layer, will provide for one's total focusing needs.

It has been discovered that the electro-active layer allows for the utilization of adaptive optic correction-like techniques to maximize one's vision through his or her electro-active lenses either prior or after final fabrication. This can be accomplished by way of allowing the patient or intended wearer to look through the electro-active lens or lenses and adjusting them manually, or by way of a special designed automatic refractor that almost instantly will measure conventional and/or non-conventional refractive error and will correct any remaining refractive error be it spherical, astigmatic, aberrations, etc. This technique will allow for the wearer to achieve 20/10 or better vision in many cases.

Furthermore, it should be pointed out that in certain embodiments a Fresnell power lens layer is utilized along with the single vision or multifocal or multifocal lens blank or optic as well as the electro-active layer. For example: the Fresnell layer is utilized to provide spherical power and thereby reduce lens thickness, the single vision lens optic to correct astigmatism, and the electro-active layer to correct for mid and near distance focusing needs.

As discussed above, in another embodiment a diffractive optic is utilized along with the single vision lens optic and the electro-active layer. In this approach the diffractive optic, which provides for additional focusing correction, further reduces the need for the electric power, circuitry, and thickness of the electro-active layer. Once again, the combination of any two or more of the following can be utilized in an additive manner to provide the total additive power needed for one's spectacle correction power needs. These being a Fresnell layer, conventional or non-conventional single vision or multifocal lens optic, diffractive optic layer, and electro-active layer or layers. Furthermore it is possible through an etching process to impart a shape and or effect of a diffractive or Fresnel layer into the electro-active material so as to create a non-hybrid or hybrid electro-active optic having a diffractive or Fresnel component. Also, it is possible using the electro-active lens to create not only conventional lens power, but also prismatic power.

It has also been discovered that utilizing either an approximate 22 mm or a 35 mm diameter round centered hybrid partial field specific electro-active lens design or an adjustable decentered hybrid electro-active partial field specific design being approximately 30 mm in diameter it is possible to minimize the electrical power circuitry needs, battery life, and battery size, reducing manufacturing costs and improving optical transparency of the final electro-active spectacle lens.

In one inventive embodiment, the decentered partial field specific electro-active lens is located so that the optical center of this field is located approximately 5 mm below the optical center of the single vision lens, while at the same time having the near working distance electro-active partial field being decentered nasally or temporally to satisfy the patient's correct near to intermediate working range pupillary distance. It should be noted that such a design approach is not limited to a circular design but could be virtually any shape that allowed the proper electro-active visual field area needed for one's vision needs. For example, the design could be oval, rectangular, square shaped, octagonal, partially curved, etc. What is important is the proper placement of the viewing area for either the hybrid partial field specific designs or hybrid full field designs that have the ability to achieve partial fields as well as non-hybrid full field designs that also have the ability to achieve partial fields.

Further it has been discovered that the electro-active layer in many cases (but not all) is utilized having an uneven thickness. That is, the metallic and conductive surrounding layers are not parallel and the gel polymer thickness varies to create a convergent or divergent lens shape. It is possible to employ such a non-uniform thickness electro-active layer in a non-hybrid embodiment or in a hybrid mode with a single vision or multifocal lens optic. This presents a wide variety of adjustable lens powers through various combinations of these fixed and electrically adjustable lenses. In some inventive embodiments, the single interconnect electro-active layer utilizes non-parallel sides creating a non-uniform thickness of the electro-active structure. However, in most inventive embodiments, but not all, the multi-grid electro-active structure utilizes a parallel structure, which creates a uniform thickness of the electro-active structure.

To illustrate some of the possibilities, a convergent single vision lens optic may be bonded to a convergent electro-active lens to create a hybrid lens assembly. Depending upon the electro-active lens material used, the electrical voltage may either increase or reduce the refractive index. Adjusting the voltage up to reduce the index of refraction would change the final lens assembly power to give less plus power, as shown in the first row of Table 1 for different combinations of fixed and electro-active lens power. If adjusting the applied voltage up increases the index of refraction of the electro-active lens optic, the final hybrid lens assembly power changes as shown in Table 2 for different combinations of fixed and electro-active lens power. It should be noted that, in this embodiment of the invention, only a single applied voltage difference is required across the electro-active layer.

TABLE 1

| S.V. or M.F. Lens Optic (Distance Vision) | Electro-Active Lens Power | Voltage Change | Index of Refractive Change | Final Hybrid Lens Assembly Power |
|---|---|---|---|---|
| + | + | − | − | Less Plus |
| + | − | − | − | More Plus |
| − | + | − | − | More Minus |
| − | − | − | − | Less Minus |

TABLE 2

| S.V. or M.F. Lens Optic (Distance Vision) | Electro-Active Lens Power | Voltage Change | Index of Refractive Change | Final Hybrid Lens Assembly Power |
|---|---|---|---|---|
| + | + | − | − | More Plus |
| + | − | − | − | Less Plus |
| − | + | − | − | Less Minus |
| − | − | − | − | More Minus |

A possible manufacturing process for such a hybrid assembly follows. In one example, the electro-active polymer gel layer can be injection-molded, cast, stamped, machined, diamond turned, and/or polished into a net lens optic shape. The thin metallic layer is deposited onto both sides of the injection molded or cast polymer gel layer by, for example, sputtering or vacuum deposition. In another exemplary embodiment, the deposited thin metallic layer is placed on both the lens optic and the other side of the injection-molded or cast electro-active material layer. A conductive layer may not be necessary, but if it is, it may also be vacuum deposited or sputtered onto the metallic layer.

Unlike conventional bifocal, multifocal or progressive lenses where the near vision power segments need to be positioned differently for different multifocal designs the invention can always be placed in one common location. For unlike different static power zones utilized by the conventional approach, where the eye moves and the head tilts to utilize such zone or zones, the present invention allows one to either look straight ahead or slightly up or down, and the entire electro-active partial or full field adjusts to correct for the necessary near working distance. This reduces eye fatigue and head and eye movements. Furthermore, when one needs to look to the distance the adjustable electro-active layer adjusts to the correct power needed to clearly see the distant object. In most cases, this would cause the electro-active adjustable near working distance field to become of plano power, thus converting or adjusting the hybrid electro-active lens back to a distance vision correction lens or low power multifocal progressive lens correcting distance power. However, this is not always the case.

In some cases it may be advantageous to reduce the thickness of the single vision lens optic. For example, the central thickness of a plus lens, or the edge thickness of a minus lens, can be reduced by way of some appropriate distance power compensation in the electro-active adjustable layer. This would apply to a full field or mostly full field hybrid electro-active spectacle lens or in all cases of a non-hybrid electro-active spectacle lens.

Once again, it should be pointed out that the adjustable electro-active layer does not have to be located in a limited area but could cover the entire single vision or multifocal lens optic, whatever size area or shape is required of either one. The exact overall size, shape, and location of the electro-active layer is constrained only due to performance and aesthetics.

It has also been discovered and is part of the invention that by utilizing the proper front convex and back concave curves of the single vision or multifocal lens blank or optic it is possible to further reduce the complexity of electronics needed for the invention. By way of properly selecting the front convex base curves of the single vision or multifocal lens blank or optic it is possible to minimize the number of connecting electrodes needed to activate the electro-active layer. In some embodiments, only two electrodes are required as the entire electro-active field area is adjusted by a set amount of electrical power.

This occurs due to the change of refractive index of the electro-active material, which creates, depending upon the placement of the electro-active layer, a different power front, back, or middle electro-active layer. Thus the appropriate curvature relationship of the front and back curves of each layer influences the needed power adjustment of the electro-active hybrid or non-hybrid lens. In most, but not all, hybrid designs especially those not utilizing a diffractive or Fresnel component it is important that the electro-active layer does not have its front & back curves parallel to that of the single vision or multifocal semifinished blank or single vision or multifocal finished lens blank it is attached to. One exception to this is a hybrid design utilizing a multi-grid structure.

It should be pointed out that one embodiment is of a hybrid electro-active lens utilizing less than a full field approach and a minimum of two electrodes. Other embodiments utilize a multi-grid electro-active layer approach to create the electro-active layer in which case multiple electrodes and electrical circuitry will be required. When utilizing a multi-grid electro-active structure, it has been discovered that for the boundaries of the grids that have been electrically activated to be cosmetically acceptable (mostly invisible), it may be necessary to produce a refractive index differential between adjacent grids of zero to 0.02 units of refractive index difference. Depending upon cosmetic demands, the range of refractive index differential could be from 0.01 to 0.05 units of refractive index differential but in most inventive embodiments the difference is limited, by way of a controller to a maximum of 0.02 or 0.03 units of refractive index difference between adjacent areas.

It is also possible to utilize one or more electro-active layers having different electro-active structures such as a single-interconnect structure and/or a multi-grid structure, which can react as needed once energized to create the desired additive end focusing power. For example only, one could correct for distance power of a full field by way of the anterior (electro-active layer, distal with respect to the wearer's eyes) and utilize the posterior (i.e. proximal) electro-active layer to focus for near vision range utilizing a partial field specific approach generated by the posterior layer. It should become readily apparent that utilizing this multi electro-active layer approach will allow for increased flexibility while keeping the layers extremely thin and reducing the complexity of each individual layer. Furthermore, this approach allows for sequencing the individual layers in as much as one can energize them all at one time, to generate a simultaneous variable additive focusing power effect. This variable focusing effect can be produced in a time lapsed sequence, so as to correct for mid-range focusing needs and near vision range focusing needs as one looks from far to near and then create the reverse effect as one looks from near to far.

The multi electro-active layer approach also allows for faster electro-active focusing power response time. This happens due to a combination of factors, one being the reduced electro-active material thickness needed for each layer of multi electro-active layered lens. Also, because a multi electro-active layer lens allows for breaking up the complexity of a master electro-active layer into two or more less complex individual layers which are asked to do less individually than the master electro-active layer.

The following describes the materials and construction of the electro-active lens, its electrical wiring circuitry, the electrical power source, the electrical switching technique, software required for focal length adjustment, and object distance ranging.

Figure 19:
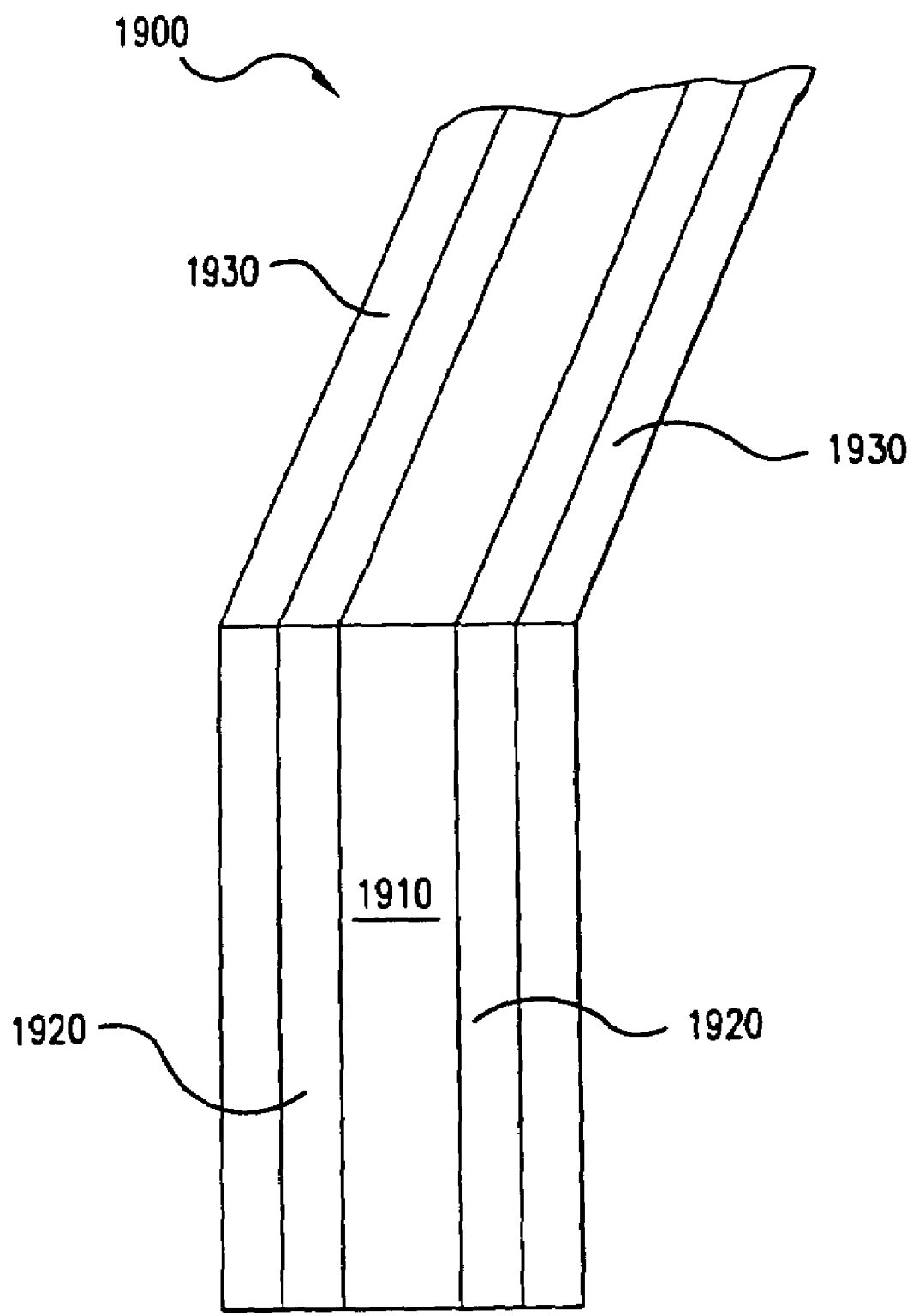
FIG. 19 is a perspective view of an embodiment of an electro-active layer 1900.

FIG. 19 is a perspective view of an exemplary embodiment of an electro-active layer 1900. Attached to both sides of an electro-active material 1910 are metallic layers 1920. Attached to the opposite side of each metallic layer 1920 are conductive layers 1930.

The electro-active layer discussed above is a multilayer construction consisting of either a polymer gel or liquid crystal as the electro-active material. However, in certain inventive cases both a polymer gel electro-active layer and a liquid crystal electro-active layer are utilized within the same lens. For example: the liquid crystal layer may be utilized to create an electronic tint or sunglass effect and the polymer gel layer may be utilized to add or subtract power. Both the polymer gel and liquid crystal has the property that its optical index of refraction can be changed by an applied electric voltage. The electro-active material is covered by two nearly transparent metallic layers on either side, and a conductive layer is deposited on each metallic layer to provide good electrical connection to these layers. When a voltage is applied across the two conductive layers, an electric field is created between them and through the electro-active material, changing the refractive index. In most cases, the liquid crystal and in some cases the gels are housed in a sealed encapsulating envelope of a material selected from silicones, polymethacrylate, styrene, proline, ceramic, glass, nylon, mylar and others.

Figure 20:
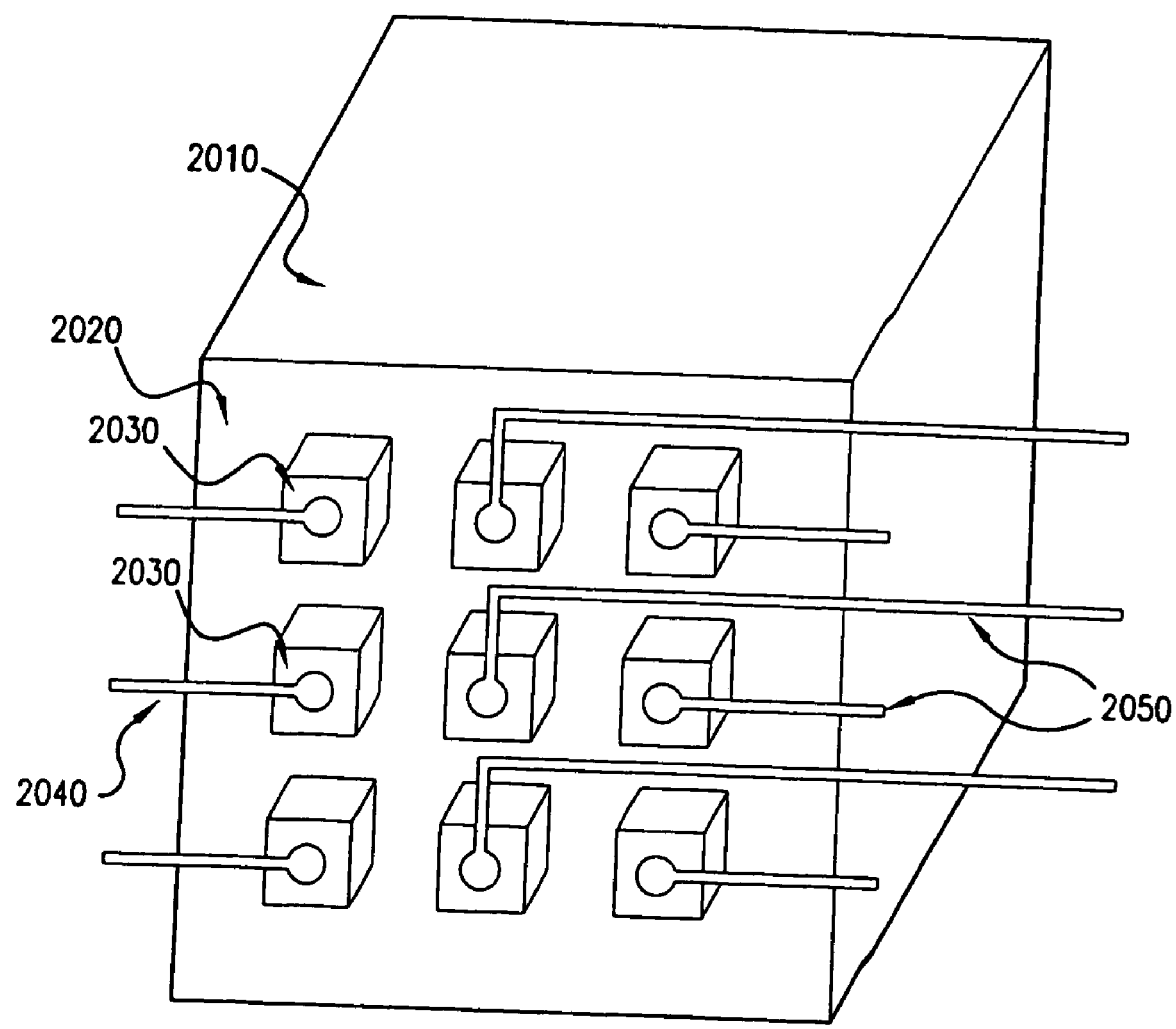
FIG. 20 is a perspective view of an embodiment of an electro-active lens 2000.

FIG. 20 is a perspective view of an embodiment of an electro-active lens 2000 having a multi-grid structure. Lens 2000 includes an electro-active material 2010 that can, in some embodiments, define a plurality of pixels, each of which can be separated by a material having electrical insulating properties. Thus, electro-active material 2010 can define a number of adjacent zones, each zone containing one or more pixels.

Attached to one side of electro-active material 2010 is a metallic layer 2020, which has a grid array of metallic electrodes 2030 separated by a material (not shown) having electrical insulating properties. Attached to the opposite side (not shown) of electro-active material 2010 is a symmetrically identical metallic layer 2020. Thus, each electro-active pixel is matched to a pair of electrodes 2030 to define a grid element pair.

Attached to metallic layer 2020 is a conductive layer 2040 having a plurality of interconnect vias 2050 each separated by a material (not shown) having electrical insulating properties. Each interconnect via 2050 electrically couples one grid element pair to a power supply and/or controller. In an alternative embodiment, some and/or all of interconnect vias 2050 can connect more than one grid element pair to a power supply and/or controller.

It should be noted that in some embodiments, metallic layer 2020 is eliminated. In other embodiments, metallic layer 2020 is replaced by an alignment layer.

In certain inventive embodiments the front (distal) surface, intermediate surface, and/or back surface can be made of a material comprising a conventional photochromatic component. This photochromatic component may or may not be utilized with an electronic produced tint feature associated as part of the electro-active lens. In the event that it is utilized it would provide an additive tint in a complimentary manner. It should be pointed out, however, in many inventive embodiments the photochromatic material is used solely with the electro-active lens without an electronic tint component. The photochromatic material can be included in an electro-active lens layer by way of the layer composition or added later to the electro-active layer or added as part of an outer layer either on the front or the back of the lens. Furthermore, the electro-active lenses of the invention can be hard-coated front, back, or both can be coated with an anti-reflection coating as desired.

This construction is referred to as a sub-assembly and it can be electrically controlled to create either a prismatic power, sphere power, astigmatic power correction, aspheric correction, or aberration correction of the wearer. Furthermore, the subassembly can be controlled to mimic that of a Fresnell or diffractive surface. In one embodiment, if more than one type of correction is needed, two or more subassemblies can be juxtaposed, separated by an electrically insulating layer. The insulating layer may be comprised of silicone oxide. In another embodiment, the same subassembly is utilized to create multiple power corrections. Either of the two sub-assembly embodiments just discussed can be made of two different structures. This first structural embodiment allows that each of the layers, the electro-active layer, conductor, and metal, are contiguous, that is, continuous layers of material, thus forming a single-interconnect structure. The second structural embodiment (as shown in FIG. 20) utilizes metallic layers in the form of a grid or array, with each sub-array area electrically insulated from its neighbors. In this embodiment showing a multi-grid electro-active structure, the conductive layers are etched to provide separate electrical contacts or electrodes to each sub-array or grid element. In this manner, separate and distinct voltages may be applied across each grid element pair in the layer, creating regions of different index of refraction in the electro-active material layer. The details of design, including layer thickness, index of refraction, voltages, candidate electro-active materials, layer structure, number of layers or components, arrangement of layers or components, curvature of each layer and/or components is left for the optical designer to decide.

It should be noted that either the multi-grid electro-active structure or the single interconnect electro-active structures can be utilized as either a partial lens field or a full lens field. However, when a partial field specific electro-active layer is utilized, in most cases, an electro-active material having a closely matching refractive index as that of the partial field specific electro-active non-activated layer (the framing layer) is utilized laterally adjacent to and separated from the partial field specific electro-active region by an insulator. This is done to enhance the cosmetic nature of the electro-active lens by way of keeping the appearance of the entire electro-active layer appearing as one, in the unactivated state. Also, it should be pointed out that in certain embodiments, the framing layer is of a non-electro-active material.

The polymer material can be of a wide variety of polymers where the electro-active constituent is at least 30% by weight of the formulation. Such electro-active polymer materials are well known and commercially available. Examples of this material include liquid crystal polymers such as polyester, polyether, polyamide, (PCB) penta cyano biphenyl and others. Polymer gels may also contain a thermoset matrix material to enhance the processability of the gel, improve its adhesion to the encapsulating conductive layers, and improve the optical clarity of the gel. By way of examples only this matrix may be a cross-linked acrylate, methacrylate, polyurethane, a vinyl polymer cross-linked with a difunctional or multifunctional acrylate, methacrylate or vinyl derivative.

The thickness of the gel layer can be, for example, between about 3 microns to about 100 microns, but may be as thick as one millimeter, or as another example, between about 4 microns to about 20 microns. The gel layer can have a modulus of, for example, about 100 pounds per inch to about 800 pounds per inch, or as another example, 200 to 600 pounds per inch. The metallic layer can have a thickness of, for example, about $10^{-4}$ microns to about $10^{-2}$ microns, and as another example, from about $0.8\times10^{-3}$ microns to about $1.2\times10^{-3}$ microns. The conductive layer can have a thickness of, for example, on the order of 0.05 microns to about 0.2 microns, and as another example, from about 0.8 microns to about 0.12 microns, and as yet another example, about 0.1 microns.

The metallic layer is used to provide good contact between the conductive layer and the electro-active material. Those skilled in the art will readily recognize the appropriate metal materials that could be used. For example, one could use gold or silver.

In one embodiment, the refractive index of the electro-active material may vary, for example, between about 1.2 units and about 1.9 units, and as another example, between about 1.45 units and about 1.75 units, with the change in index of refraction of at least 0.02 units per volt. The rate of change in the index with voltage, the actual index of refraction of the electro-active material, and its compatibility with the matrix material will determine the percentage composition of the electro-active polymer into the matrix, but should result in a change of index of refraction of the final composition of no less than 0.02 units per volt at a base voltage of about 2.5 volts but no greater than 25 volts.

As previously discussed with the inventive embodiment utilizing a hybrid design, the sections of the electro-active layer assembly are attached to a conventional lens optic with an appropriate adhesive or bonding technique which is transparent to visible light. This bonding assembly can be by way of release paper or film having the electro-active layer pre-assembled and attached ready for bonding to the conventional lens optic. It could be produced and applied to the awaiting lens optic surface in-situ. Also, it could be applied pre-applied to the surface of a lens wafer, which is then adhesively bonded to the awaiting lens optic. It could be applied to a semi-finished lens blank which is later surfaced or edged for the appropriate size, shape as well as the appropriate total power needs. Finally, it could be casted onto a preformed lens optic utilizing SurfaceCasting techniques. This creates the electrically modifiable power of the invention. The electro-active layer may occupy the entire lens area or only a portion of it.

The index of refraction of the electro-active layers can be correctly altered only for the area needed to focus. For example, in the hybrid partial field design previously discussed, the partial field area would be activated and altered within this area. Therefore, in this embodiment the index of refraction is altered in only a specific partial region of the lens. In another embodiment, that of a hybrid full field design, the index of refraction is altered across the entire surface. Similarly, the index of refraction is altered across the entire area in the non-hybrid design. As discussed earlier, it has been discovered that in order to maintain an acceptable optical cosmetic appearance the refractive index differential between adjacent areas of an electro-active optic should be limited to a maximum of 0.02 units to 0.05 units of refractive index differential, preferably 0.02 units to 0.03 units.

It is envisioned within the invention that in some cases the user would utilize a partial field and then want to switch the electro-active layer to a full field. In this case, the embodiment would be designed structurally for a full field embodiment; however, the controller would be programmed to allow for switching the power needs from a full field to a partial field and back again or vice versa.

In order to create the electric field necessary to stimulate the electro-active lens, voltage is delivered to the optical assemblies. This is provided by bundles of small diameter wires, which are contained in the edges of the frames of the spectacles. The wires run from a power source described below into the an electro-active eyewear controller, and/or one or more controller components, and to the frame edge surrounding each spectacle lens, where state-of-the-art wire bonding techniques used in semiconductor manufacturing link the wires to each grid element in the optical assembly. In the single wire interconnect structured embodiment, meaning one wire per conductive layer, only one voltage per spectacle lens is required and only two wires would be necessary for each lens. The voltage would be applied to one conductive layer, while its partner on the opposing side of the gel layer is held at ground potential. In another embodiment, an alternating current (AC) voltage is applied across opposing conductive layers. These two connections are easily made at or near the frame edge of each spectacle lens.

If a grid array of voltages is used, each grid sub-area in the array is addressed with a distinct voltage, and conductors connect each wire lead in the frame to a grid element on the lens. An optically transparent conducting material such as indium oxide, tin oxide, or indium tin oxide (ITO) may be used to form the conductive layer of the electro-active assembly which is used to connect the wires in the frame edges to each grid element in the electro-active lens. This method can be used regardless of whether the electro-active area occupies the entire lens region or only a portion of it.

To provide electric power to the optical assemblies, a source of electricity, such as a battery, is included in the design. The voltages to create the electric field are small, hence, the temples of the frames are designed to allow for the insertion and extraction of miniature bulk batteries which provide this power. The batteries are connected to the wire bundles through a multiplexing connection also contained in the frame temples. In another embodiment, conformal thin film batteries are attached to the surface of the frame temples with an adhesive that allows them to be removed and replaced when their charge is dissipated. An alternative would be to provide an AC adapter with an attachment to the frame-mounted batteries to allow in situ charging of either the bulk or conformal thin-film batteries when not in use.

An alternate energy source is also possible whereby a miniature fuel cell could be included in the spectacle frames to provide greater energy storage than batteries. The fuel cell could be recharged with a small fuel canister that injects fuel into a reservoir in the spectacle frames.

It has been discovered that it is possible to minimize the electrical power needs by way of utilizing an inventive hybrid multi-grid structure approach which comprises in most cases but not all, a partial field specific region. It should be pointed out, while one can utilize a hybrid partial field multi-grid structure, a hybrid full field multi-grid structure can be utilized as well.

In another inventive approach, whereby non-conventional refractive error such as aberrations are corrected, a tracking system is built into the eyewear, such as discussed above, and the proper enabling software and programming of the electro-active eyewear controller, and/or one or more controller components, housed in the electro-active eyewear is provided. This inventive embodiment both tracks one's line of sight, by way of tracking one's eyes, and applies the necessary electrical energy to the specific area of the electro-active lens being looked through. In other words, as the eyes move a targeted electrically energized area would move across the lens corresponding to one's line of sight directed through the electro-active lens. This would be manifested in several different lens designs. For example, the user could have a fixed power lens, an electro-active lens, or a hybrid of both types to correct for conventional (sphere, cylinder, and prism) refractive error. In this example, the non-conventional refractive error would be corrected by way of the electro-active layer being of a multi-grid structure whereby, as the eye moves the corresponding activated region of the electro-active lens would move with the eye. In other words, the eye's line-of-sight corresponding to the eye's movement, as it intersects the lens would move across the lens in relationship to the eye's movements.

In the above inventive example it should be pointed out that the multi-grid electro-active structure, which is incorporated into or on the hybrid electro-active lens can be of a partial field or a full field design.

It should be pointed out utilizing this inventive embodiment one can minimize the electrical needs by way of only electrically energizing the limited area being directly viewed through. Therefore, the smaller area being energized the less electrical power consumed for a given prescription at any one time. The non directly viewed area would, in most cases but not all, not be energized or activated and therefore, would correct for conventional refractive error that would get one to 20/20 vision correcting for example, myopia, hyperopia, astigmatism, and presbyopia. The targeted and tracked area in this inventive embodiment would correct for as much non-conventional refractive error as possible, that being irregular astigmatism, aberrations, and ocular surface or layer irregularities. In other inventive embodiments the targeted and tracked area could correct for also some conventional error, as well. In several of the previous mentioned embodiments, this targeted and tracked area can be automatically located with the assistance of the controller, and/or one or more controller components, by way of either a range finder located in the eyewear tracking the eye movements, with a eye tracking system located in the eyewear or both a tracking system and a range finder system.

Although only a partial electro-active region is utilized in certain designs, the entire surface is covered with the electro-active material to avoid a circular line visible to the user in the lens in the nonactivated state. In some inventive embodiments, a transparent insulator is utilized to keep the electrical activation limited to the central area being activated and the unactivated peripheral electro-active material is utilized to keep the edge of the active region invisible.

In another embodiment, thin film solar cell arrays can be attached to the surface of the frames, and voltage is supplied to the wires and the optical grid by photoelectric effect using sunlight or ambient room lighting. In one inventive embodiment, solar arrays are used for primary power, with the miniature batteries discussed earlier included as back up power. When electrical power is not needed the batteries can be charged from the solar cells during these times in this embodiment. An alternative allows for an AC adapter and attachment to batteries with this design.

In order to provide a variable focal length to the user, the electro-active lenses are switchable. At least two switch positions are provided, however, more are provided if needed. In the simplest embodiment, the electro-active lenses are either on or off. In the off position, no current flows through the wires, no voltage is applied to the grid assemblies, and only the fixed lens power is utilized. This would be the case in a user requiring a far field distance correction, for example, assuming of course, the hybrid electro-active lens utilizes either a single vision or multifocal lens blank or optic which corrects for distance vision as part of its construction. To provide near vision correction for reading, the switch would be on, providing a predetermined voltage or array of voltages to the lenses, creating a positive add power in the electro-active assemblies. If a mid-field correction is desired, a third switch position can be included. The switch could be microprocessor controlled, or manually user controlled. In fact, there could be several additional positions included. In another embodiment, the switch is analog not digital, and provides continuous variance of the focal length of the lens by adjusting a knob or lever much like a volume control on a radio.

It may be the case that no fixed lens power is part of the design, and all vision correction is accomplished via the electro-active lens. In this embodiment, a voltage or array of voltages is supplied to the lens at all times if both a distance and near vision correction is needed by the user. If only a distance correction or reading accommodation is needed by the user, the electro-active lens would be on when correction is needed and off when no correction is needed. However, this is not always the case. In certain embodiments depending upon the lens design, turning off or down the voltage will automatically increase the power of the distance and or near vision zones.

In one exemplary embodiment, the switch itself is located on the spectacle lens frames and is connected to a controller, for example, an Application Specific Integrated Circuit, contained in the spectacle frames. This controller responds to different positions of the switch by regulating the voltages supplied from the power source. As such, this controller makes up the multiplexer discussed above, which distributes various voltages to the connecting wires. The controller may also be of an advanced design in the form of a thin film and be mounted like the battery or solar cells conformably along the surface of the frames.

In one exemplary embodiment, this controller, and/or one or more controller components, is fabricated and/or programmed with knowledge of the user's vision correction requirements, and allows the user to easily switch between different arrays of pre-determined voltages tailored for his or her individual vision requirements. This electro-active eyewear controller, and/or one or more controller components, is easily removable and/or programmable by the vision care specialist or technician and replaced and/or reprogrammed with a new "prescription" controller when the user's vision correction requirements change.

One aspect of the controller-based switch is that it can change the voltage applied to an electro-active lens in less than a microsecond. If the electro-active layer is manufactured from a fast-switching material, it is possible that the rapid change in focal length of the lenses may be disruptive to the wearer's vision. A gentler transition from one focal length to another may be desirable. As an additional feature of this invention, a "lag time" can be programmed into the controller that would slow the transition. Conversely, a "lead time" could be programmed into the controller that would speed the transition. Similarly, the transition could be anticipated by a predictive algorithm.

In any event, the time constant of the transition can be set so that it is proportional and/or responsive to the refractive change needed to accommodate the wearer's vision. For example, small changes in focusing power could be switched rapidly; while a large change in focusing power, such as a wearer quickly moving his gaze from a distant object to read printed material, could be set to occur over a longer time period, say 10–100 milliseconds. This time constant could be adjustable, according to the comfort of the wearer.

In any event, it is not necessary for the switch to be on the spectacles themselves. In another exemplary embodiment, the switch is in a separate module, possibly in a pocket in the user's clothing, and is activated manually. This switch could be connected to the spectacles with a thin wire or optical fiber. Another version of the switch contains a small microwave or radio-frequency short-range transmitter which sends a signal regarding switch position to a tiny receiver antenna mounted conformably on the spectacle frames. In both of these switch configurations, the user has direct but discreet control over the focal length variation of his or her spectacles.

In yet another exemplary embodiment, the switch is automatically controlled by a range finding device located, for example, in the frame, on the frame, in the lens, and/or on the lens of the spectacles, and pointing forward toward the object to be perceived.

Figure 21:
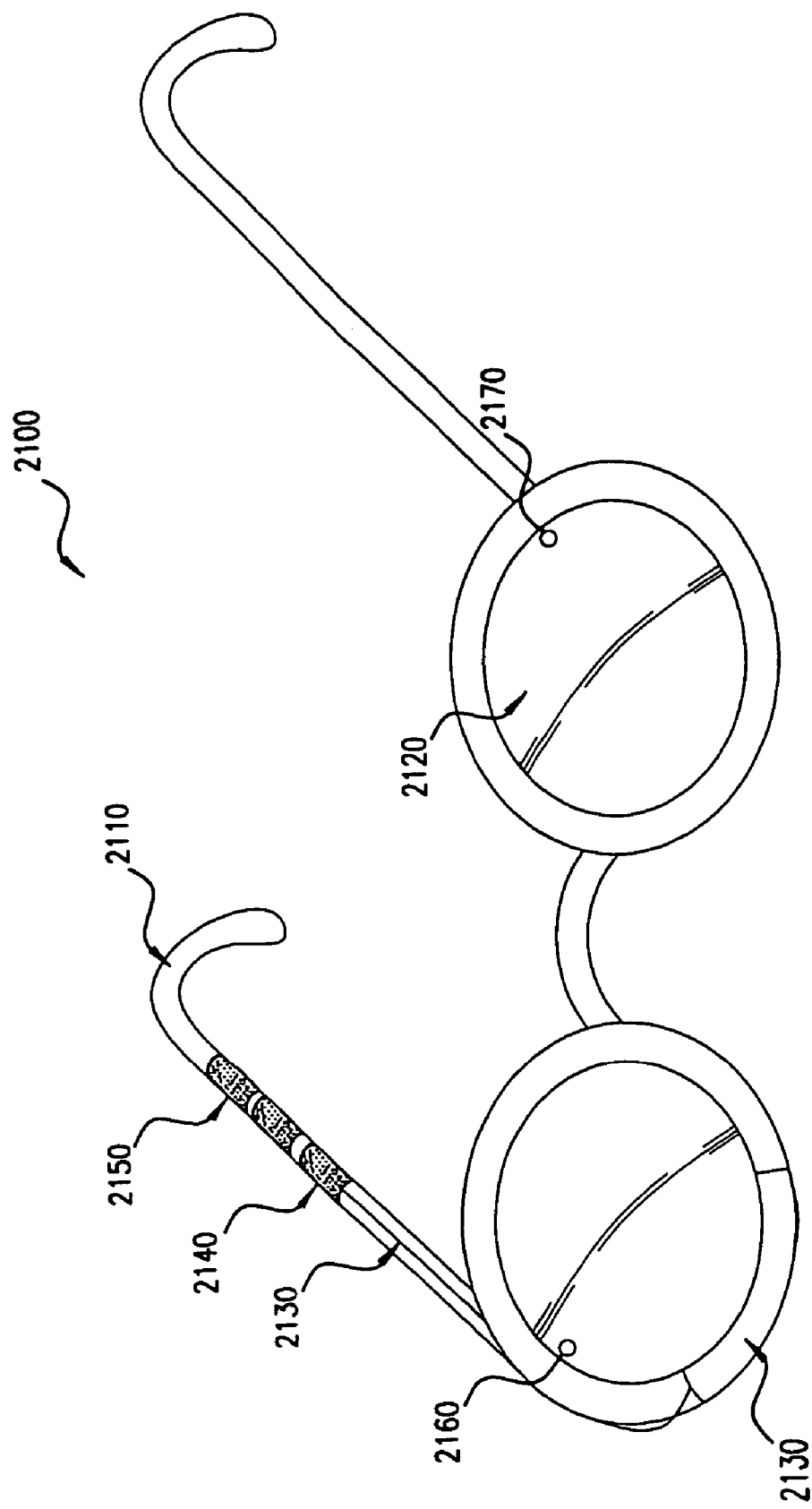
FIG. 21 is a perspective view of an embodiment of electro-active eyewear 2100.

FIG. 21 is a perspective view of another inventive embodiment of electro-active eyewear 2100. In this illustrative example, frames 2110 contain electro-active lenses 2120 that are connected by connecting wires 2130 to controller 2140 (integrated circuit) and power source 2150. A range finder transmitter 2160 is attached to an electro-active lens 2120 and a range finder receiver 2170 is attached to the other electro-active lens 2120. In various alternative embodiments, transmitter 2160 and/or receiver 2170 can be attached to any electro-active lens 2120, attached to frame 2110, embedded in lens 2120, and/or embedded in frame 2110. Further, range finder transmitter 2160 and/or receiver 2170 can be controlled by controller 2140 and/or a separate controller (not shown). Similarly, signals received by receiver 2170 can be processed by controller 2140 and/or a separate controller (not shown).

In any event, this range finder is an active seeker and can utilize various sources such as: lasers, light emitting diodes, radio-frequency waves, microwaves, or ultrasonic impulses to locate the object and determine its distance. In one embodiment, a vertical cavity surface-emitting laser (VCSEL) is used as the light transmitter. The small size and flat profile of these devices make them attractive for this application. In another embodiment, an organic light emitting diode, or OLED, is used as the light source for the rangefinder. The advantage of this device is that OLEDs can often be fabricated in a way that they are mostly transparent. Thus, an OLED might be a preferable rangefinder design if cosmetics is a concern, since it could be incorporated into the lens or frames without being noticeable.

An appropriate sensor to receive the reflected signal off the object is placed in one or more positions on the front of the lens frames and connected to a tiny controller to compute the range. This range is sent via a wire or optical fiber to the switching controller located in the lens frames or a wireless remote carried on oneself and analyzed to determine the correct switch setting for that object distance. In some cases, the ranging controller and switching controller may be integrated together.

In another exemplary embodiment, the switch can be controlled by a small but rapid movement of the user's head. This would be accomplished by including a tiny microgyroscope or micro-accelerometer in the temple on the lens frames. A small, rapid shake or twist of the head would trigger the micro-gyro or micro-accelerometer and cause the switch to rotate through its allowed position settings, changing the focus of the electro-active lens to the desired correction.

Yet another exemplary embodiment uses a combination of microgyroscope with a manual switch. In this embodiment, the microgyroscope is utilized for mostly reading and visual functions below the 180 so as to react to one's head tilt. Thus, when one's head tilts, the microgyroscope sends a signal to the controller indicating the degree of head tilt, which is then converted into increased focusing power, depending on the severity of the tilt. The manual switch, which can be remote, is used for overriding the microgyroscope for certain visual functions at or above the 180, such as working on a computer.

In still another exemplary embodiment, a combination of a rangefinder and a microgyroscope is utilized. The microgyroscope is utilized for near vision, and other vision functions below the 180, and the rangefinder is used for viewing distances which are above the 180 and are of a viewing distance of, for example, four feet or less.

As an alternative to the manual switch or range finder design to adjust the focusing power of the electro-active assembly, another exemplary embodiment utilizes an eyetracker to measure inter-pupillary distance. As the eyes focus on distant or near objects, this distance changes as the pupils converge or diverge. At least two light-emitting diodes and at least two adjacent photo-sensors to detect reflected light from the diodes off the eye are placed on the inside frame near the nose bridge. This system can sense the position of the edge of the pupil of each eye and convert the position to inter-pupillary distance to calculate the distance of the object from the user's eye plane. In certain embodiments three or even four light emitting diodes and photo sensors are used to track eye movements.

In addition to vision correction, the electro-active layer can also be used to give a spectacle lens an electro-chromic tint. By applying an appropriate voltage to an appropriate gel polymer or liquid crystal layer, a tint or sunglass effect can be imparted to the lens, which alternates the light transmission somewhat through the lens. This reduced light intensity gives a "sunglass" effect to the lens for the comfort of the user in bright, outdoor environment. Liquid crystal compositions and gel polymers with high polarizability in response to an applied electric field are most attractive for this application.

In some inventive embodiments, this invention may be used in locations where temperature variations may be sizeable enough to affect the index of refraction of the electro-active layer. Then, a correction factor to all of the supplied voltages to the grid assemblies would have to be applied to compensate for this effect. A miniature thermistor, thermocouple, or other temperature sensor mounted in or on the lens and/or frame and connected to the power source senses changes in temperature. The controller converts these readings into voltage changes needed to compensate for the change in refractive index of the electro-active material.

However, in certain embodiments electronic circuitry is actually built into or on the lens surface for the purpose of increasing the temperature of the electro-active layer or layers. This is done to further reduce the refractive index of the electro-active layers thus maximizing lens power changes. Increased temperature can be utilized either with or without voltage increases thus giving additional flexibility in being able to control and change the lens power by way of refractive index changes. When temperature is utilized it is desirable to be able to measure, get feed back and control the temperature which has been deliberately applied.

In the case of either a partial or full field grid array of individually addressed electro-active regions, many conductors may be necessary to multiplex specific voltages from the controller to each grid element. For ease of engineering these interconnects, the invention locates the controller in the front section of the spectacle frames, for example, in the nose bridge area. Thus, the power source, which is located in the temples, will be connected to the controller by only two conductors through the temple-front frame hinge. The conductors linking the controller to the lenses can be totally contained within the front section of the frame.

In some embodiments of the invention, the spectacles may have one or both spectacle frame temples, parts of which are easily removable. Each temple will consist of two parts: a short one which remains connected to the hinge and front frame section and a longer one which plugs into this piece. The unpluggable part of the temples each contain an electrical power source (battery, fuel cell, etc.) and can be simply removed and reconnected to the fixed portion of the temples. These removable temples are rechargeable, for example, by placing in a portable A.C. charging unit which charges by direct current flow, by magnetic induction, or by any other common recharging method. In this manner, fully charged replacement temples may be connected to the spectacles to provide continuous, long-term activation of the lenses and ranging system. In fact, several replacement temples may be carried by the user in pocket or purse for this purpose.

In many cases, the wearer will require spherical correction for distance, near, and/or intermediate vision. This allows a variation of the fully interconnected grid array lens, which takes advantage of the spherical symmetry of the required corrective optic. In this case a special geometrically shaped grid consisting of concentric rings of electro-active regions may comprise either the partial region or full field lens. The rings may be circular or non circular such as, for example, elliptical. This configuration serves to reduce substantially the number of required electro-active regions that must be separately addressed by conductor connections with different voltages, greatly simplifying the interconnect circuitry. This design allows for the correction of astigmatism by employing a hybrid lens design. In this case, the conventional optic may provide cylindrical and/or astigmatic correction, and the concentric ring electro-active layer may provide the spherical distance and/or near vision correction.

This concentric ring, or toroidal zone, embodiment allows for great flexibility in adapting the electro-active focusing to the wearer's needs. Because of the circular zone symmetry, many more thinner zones can be fabricated without increasing the wiring and interconnect complexity. For example, an electro-active lens made from an array of 4000 square pixels will require wiring to address all 4000 zones; a need to cover a circular partial region area of 35 millimeters diameter will yield a pixel pitch of about 0.5 millimeters. On the other hand, an adaptive optic made from a pattern of concentric rings of the same 0.5 millimeter pitch (or ring thickness) will require only 35 toroidal zones, greatly reducing the wiring complexity. Conversely, the pixel pitch (and resolution) can be decreased to only 0.1 millimeters and only increase the number of zones (and interconnects) to 175. The greater resolution of the zones may translate into greater comfort for the wearer, since the radial change in refractive index from zone to zone is smoother and more gradual. Of course, this design restricts one to only vision corrections which are spherical in nature.

It has been further discovered that the concentric ring design can tailor the thickness of the toroidal rings so as to place the greatest resolution at the radius where it is needed. For example, if the design calls for phase-wrapping, i.e., taking advantage of the periodicity of light waves to achieve greater focusing power with materials of limited refractive index variation, one can design an array with narrower rings at the periphery and wider rings at the center of the circular partial region of the electro-active area. This judicious use of each toroidal pixel yields the greatest focusing power obtainable for the number of zones utilized while minimizing the aliasing effect present in low resolution systems that employ phase-wrapping.

In another embodiment of this invention, it may be desired to smooth the sharp transition from the far-field focus region to the near vision focus region in hybrid lenses employing a partial electro-active area. This occurs, of course, at the circular boundary of the electro-active region. In order to accomplish this, the invention would be programmed to have regions of less power for near vision in the periphery of the electro-active region. For example, consider a hybrid concentric ring design with a 35 mm diameter electro-active region, where the fixed focal length lens provides a distance correction, and the electro-active region provides a +2.50 add power presbyopic correction. Instead of maintaining this power all the way out to the periphery of the electro-active region, several toroidal regions or "bands", each containing several addressable electro-active concentric ring zones, would be programmed to have decreasing power at larger diameters. For example, during activation one embodiment might have a central 26 mm diameter circle of +2.50 add power, with a toroidal band extending from 26 to 29 mm diameter with +2.00 add power, another toroidal band extending from 29 to 32 mm diameter with +1.5 add power, surrounded by a toroidal band extending from 32 to 35 mm diameter with +1.0 add power. This design may be useful in providing some users with a more pleasant wearing experience.

When utilizing an ophthalmic spectacle lens one generally utilizes the top approximately one-half of the lens for far distance viewing. Approximately 2 to 3 mm above the mid-line and 6 to 7 mm below the mid-line for intermediate distance viewing and from 7–10 mm below the mid-line for near distance viewing.

Aberrations created in the eye appear different for distances from the eye and need to be corrected differently. An object's distance that is being viewed is directly related to the specific aberration correction needed. Therefore, an aberration created from the eye's optical system will need approximately the same correction for all far distances, approximately the same correction for all intermediate distances, and approximately the same correction for all near point distances. Therefore, the invention allows for the electro-active adjustment of the lens to correct certain aberrations of the eye, in three or four sections of the lens (distance section, intermediate section and near section), as opposed to trying to adjust the electro-active lens grid-by-grid as the eye and the eye's line of sight moves across the lens.

Figure 22:
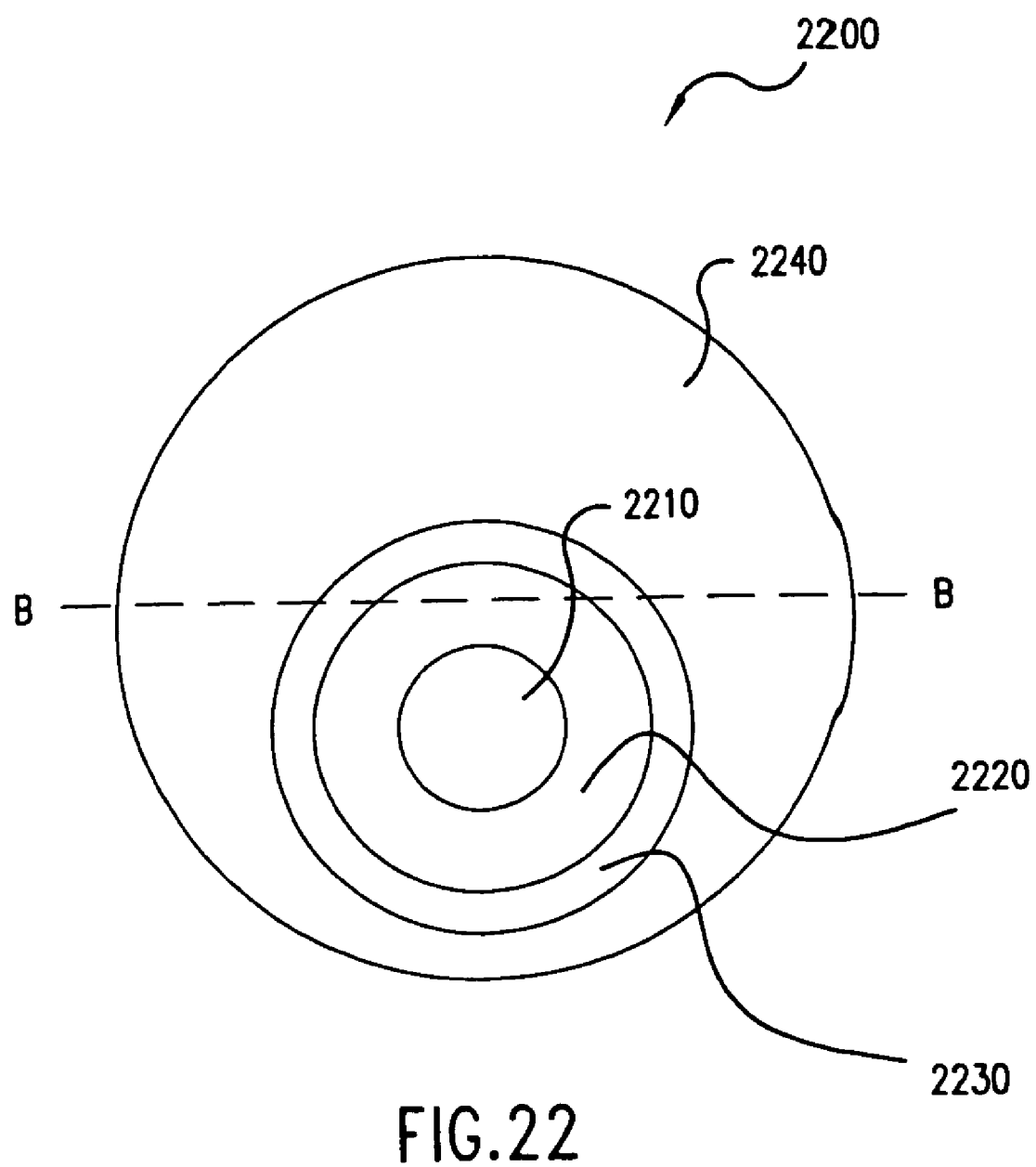
FIG. 22 is a front view of an embodiment of an electro-active lens 2200.

FIG. 22 is a front view of an embodiment of an electro-active lens 2200. Within lens 2200 are defined various regions proving different refractive corrections. Below mid-line B—B, several near distance corrective regions 2210 and 2220 each having a different corrective power, are surrounded by a single intermediate distance corrective region 2230. Although only two near distance corrective regions 2210 and 2220 are shown, any number of near distance corrective regions can be provided. Similarly, any number of intermediate distance corrective regions can be provided. Above mid-line B—B, a far distance corrective region 2240 are provided. Regions 2210, 2220, and 2230 can be activated in a programmed sequence manner, to save power for example, or in a static on-off manner similar to a conventional tri-focal. When looking from far to near, or from near to far, lens 2200 can help the wearer's eye focus, by smoothing the transition between the various focal lengths of the various regions. Thereby, the phenomenon of "image jump" is relieved or greatly reduced. This improvement is also provided in the embodiments shown in FIGS. 23 and 24, below.

Figure 23:
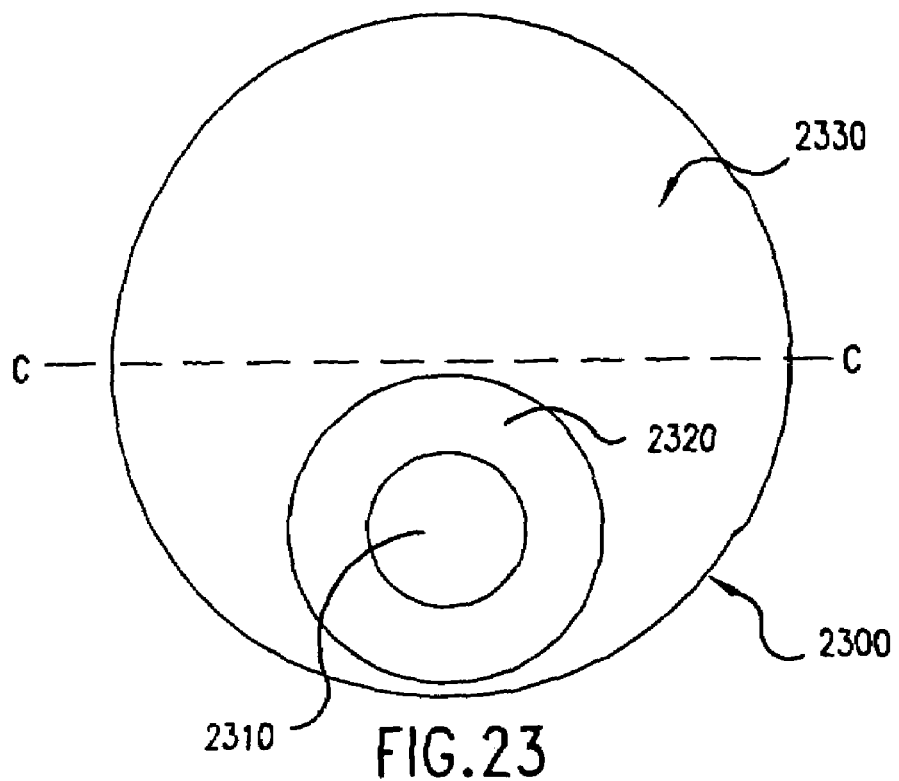
FIG. 23 is a front view of an embodiment of an electro-active lens 2300.

FIG. 23 is a front view of an embodiment of another electro-active lens 2300. Within lens 2300 are defined various regions proving different refractive corrections. Below mid-line C—C, a single near distance corrective region 2310 is surrounded by a single intermediate distance corrective region 2320. Above mid-line C—C, is located a single far distance corrective region 2330.

Figure 24:
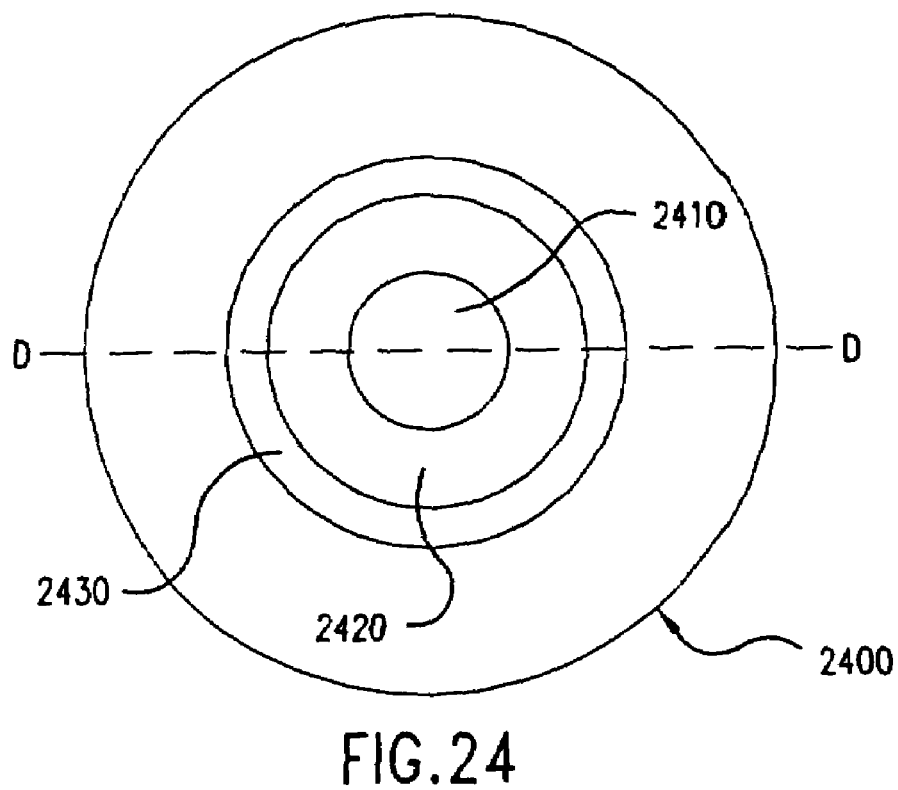
FIG. 24 is a front view of an embodiment of an electro-active lens 2400.

FIG. 24 is a front view of an embodiment of an embodiment of another electro-active lens 2400. Within lens 2400 are defined various regions providing different refractive corrections. A single near distance corrective region 2410 is surrounded by a single intermediate distance corrective region 2420, which is surrounded by a single far distance corrective region 2430.

Figure 25:
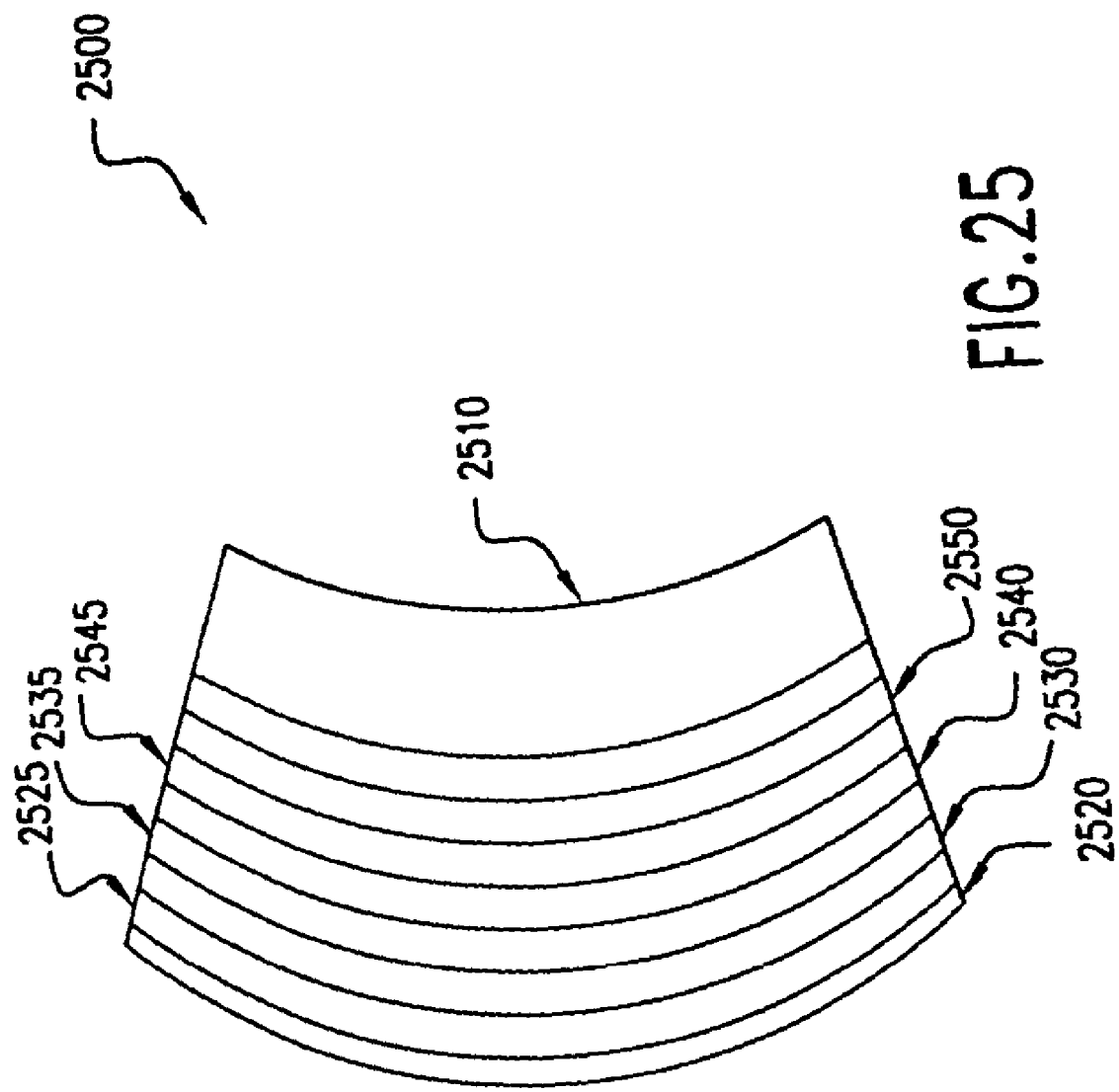
FIG. 25 is a section view of an embodiment of an electro-active lens 2500 taken along section line Z—Z of FIG. 5.

FIG. 25 is a side view of an embodiment of another electro-active lens 2500. Lens 2500 includes a conventional lens optic 2510 to which several full field electro-active regions 2520, 2530, 2540, and 2550 are attached, each separated from the adjacent regions by insulating layers 2525, 2535, and 2545.

Figure 26:
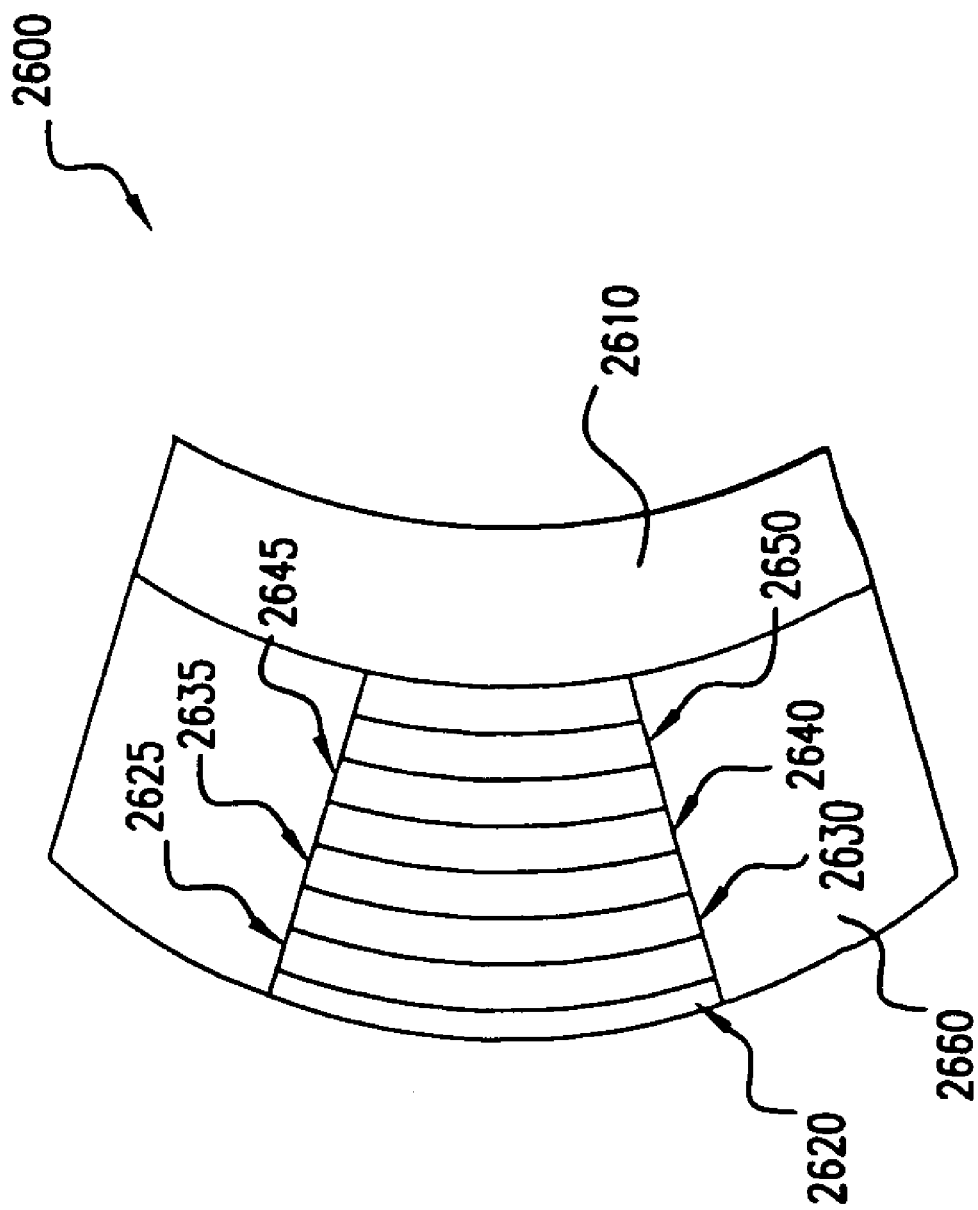
FIG. 26 is a section view of an embodiment of an electro-active lens 2600 taken along section line Z—Z of FIG. 5.

FIG. 26 is a side view of an embodiment of another electro-active lens 2600. Lens 2600 includes a conventional lens optic 2610 to which several partial field electro-active regions 2620, 2630, 2640, and 2650 are attached, each separated from the adjacent regions by insulating layers 2625, 2635, and 2645. Framing region 2660 surrounds electro-active regions 2620, 2630, 2640, and 2650.

Returning to the discussion of diffractive electro-active lenses, an electro-active lens for correcting refractive error can be fabricated using an electro-active layer adjacent to a glass, polymer, or plastic substrate lens which is imprinted or etched with a diffractive pattern. The surface of the substrate lens which has the diffractive imprint is directly in contact with the electro-active material. Thus, one surface of the electro-active layer is also a diffractive pattern which is the mirror image of that on the lens substrate surface.

The assembly acts as a hybrid lens, such that the substrate lens always provides a fixed corrective power, typically for distance correction. The index of refraction of the electro-active layer in its unactivated state is nearly identical to that of the substrate lens; this difference should be 0.05 index units or less. Thus, when the electro-active lens is unactivated, the substrate lens and electro-active layer have the same index, and the diffractive pattern is powerless, and provides no correction (0.00 diopter). In this state, the power of the substrate lens is the only corrective power.

When the electro-active layer is activated, its index changes, and the refractive power of the diffraction pattern becomes additive to the substrate lens. For example, if the substrate lens has a power of −3.50 diopter, and the electro-active diffractive layer has a power when activated of +2.00 diopter, the total power of the electro-active lens assembly is −1.50 diopter. In this way, the electro-active lens allows for near vision or reading. In other embodiments, the electro-active layer in the activated state may be index matched to the lens optic.

Electro-active layers that use liquid crystals are birefringent. That is, they display two different focal lengths in their unactivated state when exposed to unpolarized light. This birefringence gives rise to double or fuzzy images on the retina. There are two approaches to solving this problem. The first requires at least two electro-active layers to be used. One is fabricated with the electro-active molecules aligned longitudinally in the layer, while the other is fabricated with latitudinally oriented molecules in its layer; thus, the molecular alignment in the two layers is orthogonal to each other. In this manner, both polarizations of light are focused equally by both of the layers, and all light is focused at the same focal length.

This can be accomplished by simply stacking the two orthogonally-aligned electro-active layers or by an alternative design in which the center layer of the lens is a double-sided plate, i.e., with identical diffraction patterns etched on both sides. Electro-active material is then placed in a layer on both sides of the center plate, assuring that their alignments are orthogonal. Then a cover superstrate is placed over each electro-active layer to contain it. This provides a simpler design than superimposing two distinct electro-active/diffractive layers on top of each other.

A different alternative requires one to add a cholesteric liquid crystal to the electro-active material to give it a large chiral component. It has been found that a certain level of chiral concentration eliminates the in-plane polarization sensitivity, and obviates the need for two electro-active layers of purely nematic liquid crystal as a component in the electro-active material.

Turning now to the materials used for the electro-active layer, examples of material classes and specific electro-active materials that can be used for the electro-active layer and lens of the present invention are listed below. Other than the liquid crystal materials listed below in class I, we generally refer to each of these classes of materials as polymer gels.

I) Liquid Crystals

This class includes any liquid crystal film that forms nematic, smectic, or cholesteric phases that possess a long-range orientational order that can be controlled with an electric field. Examples of nematic liquid crystals are: pentyl-cyano-biphenyl (5CB), (n-octyloxy)-4-cyanobiphenyl (8OCB). Other examples of liquid crystals are the n=3, 4, 5, 6, 7, 8, 9, of the compound 4-cyano-4-n-alkylbiphenyls, 4-n-pentyloxy-biphenyl, 4-cyano-4"-n-alkyl-p-terphenyls, and commercial mixtures such as E7, E36, E46, and the ZLI-series made by BDH (British Drug House)-Merck.

II) Electro-optic Polymers

This class includes any transparent optical polymeric material such as those disclosed in "Physical Properties of Polymers Handbook" by J. E. Mark, American Institute of Physics, Woodburry, N.Y., 1996, containing molecules having unsymmetrical polarized conjugated—electrons between a donor and an acceptor group (referred to as a chromophore) such as those disclosed in "Organic Nonlinear Optical Materials" by Ch. Bosshard et al., Gordon and Breach Publishers, Amsterdam, 1995. Examples of polymers are as follows: polystyrene, polycarbonate, polymethylmethacrylate, polyvinylcarbazole, polyimide, polysilane. Examples of chromophores are: paranitroaniline (PNA), disperse red 1 (DR 1), 3-methyl-4-methoxy-4'-nitrostilbene, diethylaminonitrostilbene (DANS), diethyl-thio-barbituric acid.

Electro-optic polymers can be produced by: a) following a guest/host approach, b) by covalent incorporation of the chromophore into the polymer (pendant and main-chain), and/or c) by lattice hardening approaches such as cross-linking.

III) Polymer Liquid Crystals

This class includes polymer liquid crystals (PLCs), which are also sometimes referred to as liquid crystalline polymers, low molecular mass liquid crystals, self-reinforcing polymers, in situ-composites, and/or molecular composites. PLCs are copolymers that contain simultaneously relatively rigid and flexible sequences such as those disclosed in "Liquid Crystalline Polymers: From Structures to Applications" by W. Brostow, edited by A. A. Collyer, Elsevier, New-York-London, 1992, Chapter 1. Examples of PLCs are: polymethacrylate comprising 4-cyanophenyl benzoate side group and other similar compounds.

IV) Polymer Dispersed Liquid Crystals

This class includes polymer dispersed liquid crystals (PDLCs), which consist of dispersions of liquid crystal droplets in a polymer matrix. These materials can be made in several ways: (i) by nematic curvilinear aligned phases (NCAP), by thermally induced phase separation (TIPS), solvent-induced phase separation (SIPS), and polymerization-induced phase separation (PIPS). Examples of PDLCs are: mixtures of liquid crystal E7 (BDH-Merck) and NOA65 (Norland products, Inc. NJ); mixtures of E44 (BDH-Merck) and polymethylmethacrylate (PMMA); mixtures of E49 (BDH-Merck) and PMMA; mixture of the monomer dipentaerythrol hydroxy penta acrylate, liquid crystal E7, N-vinylpyrrolidone, N-phenylglycine, and the dye Rose Bengal.

V) Polymer Stabilized Liquid Crystals

This class includes polymer-stabilized liquid crystals (PSLCs), which are materials that consist of a liquid crystal in a polymer network in which the polymer constitutes less than 10% by weight of the liquid crystal. A photopolymerizable monomer is mixed together with a liquid crystal and an UV polymerization initiator. After the liquid crystal is aligned, the polymerization of the monomer is initiated typically by UV exposure and the resulting polymer creates a network that stabilizes the liquid crystal. For examples of PSLCs, see, for instance: C. M. Hudson et al. Optical Studies of Anisotropic Networks in Polymer-Stabilized Liquid Crystals, Journal of the Society for Information Display, vol. 5/3, 1–5, (1997), G. P. Wiederrecht et al, Photorefractivity in Polymer-Stabilized Nematic Liquid Crystals, J. of Am. Chem. Soc., 120, 3231–3236 (1998).

VI) Self-Assembled Nonlinear Supramolecular Structures

This class includes electro-optic asymmetric organic films, which can be fabricated using the following approaches: Langmuir-Blodgett films, alternating polyelectrolyte deposition (polyanion/polycation) from aqueous solutions, molecular beam epitaxy methods, sequential synthesis by covalent coupling reactions (for example: organotrichlorosilane-based self-assembled multilayer deposition). These techniques usually lead to thin films having a thickness of less than about 1_m.

Still other advantages and embodiments of the invention will become readily apparent to those skilled in this art from the above-recited detailed description. Accordingly, the drawings, descriptions, and examples provided herein are to be regarded as exemplary and illustrative in nature, and not as restrictive. For example, electro-active eyewear can be provided that has one hybrid lens and one non-hybrid lens. Similarly, electro-active eyewear can be provided that has one full field electro-active lens and one partial field electro-active lens. Likewise, electro-active eyewear can be provided that has one lens that employs a single interconnect electro-active structure and another that employs a multi-grid electro-active structure.

What is claimed is:

1. An electro-active lens comprising:
    an electro-active material of a substantially constant thickness;
    at least one alignment layer to align molecules of the electro-active material;
    a plurality of conductive electrodes arranged in a grid or array comprising a plurality of elements, wherein each grid or array element is an electrode, wherein each electrode is isolated from other electrodes by an insulating material; and
    wherein the electro-active lens is capable of being edged without destroying or removing material or components needed for the electro-active material to function properly.

2. The electro-active lens of claim 1, wherein the insulating material is an oxide.

3. The electro-active lens of claim 2, wherein the insulating material is silicon oxide.

4. The electro-active lens of claim 1, wherein the insulating material is substantially transparent.

5. The electro-active lens of claim 1, wherein the grids or arrays are substantially circular and concentric with respect to one another.

6. The electro-active lens of claim 1, wherein the electro-active material contalns a liquid crystal.

7. An electro-active lens comprising:
    at least one layer of electro-active material having substantially constant thickness;
    at least one alignment layer to align molecules of the electro-active material;
    at least one grid or array of conductive electrodes in electrical contact with the at least one layer of electro-active material, wherein each grid or array element is an electrode and wherein the optical power of the electro-active lens is varied by altering an applied voltage from a power source to individual electrodes of the grid or array, each electrode is isolated from at least one other electrode by an insulating material; and wherein the electro-active lens is capable of being edged without destroying or removing material or components needed for the electro-active material to function properly.

8. The electro-active lens of claim 7 wherein a change in refractive index of the electro-active material is at least 0.02 units per volt.

9. An ophthalmic electro-active lens comprising:

an electro-active material of a substantially constant thickness;

at least one alignment layer to align molecules of the electro-active material; and a plurality of conductive electrodes arranged in a grid or array comprising a plurality of elements, wherein each grid or array element is an electrode, wherein each electrode is isolated from other electrodes by an insulating material, wherein the electro-active material is at least partially disposed above a pupil of a wearer's eye when the ophthalmic electro-active lens is in an as-worn position, and wherein the ophthalmic electro-active lens is capable of being edged without destroying or removing material or components needed for the electro-active material to function properly.

10. The electro-active lens of claim 9, wherein the insulating material is an oxide.

11. The electro-active lens of claim 10, wherein the insulating material is silicon oxide.

12. The electro-active lens of claim 9, wherein the insulating material is substantially transparent.

13. The electro-active lens of claim 9, wherein the grids or arrays are substantially circular and concentric with respect to one another.

14. The electro-active lens of claim 9, wherein the electro-active material contains a liquid crystal.

15. An ophthalmic electro-active lens comprising:

at least one layer of electro-active material having substantially constant thickness;

at least one alignment layer to align molecules of the electro-active material;

at least one grid or array of conductive electrodes in electrical contact with the at least one layer of electro-active material, wherein each grid or array element is an electrode and wherein the optical power of the electro-active lens is varied by altering an applied voltage from a power source to individual electrodes of the grid or array, the electrodes isolated from another by an insulating material, wherein the electro-active material is at least partially disposed above a pupil of a wearer's eye when the ophthalmic electro-active lens is in an as-worn position, and wherein the ophthalmic electro-active lens is capable of being edged without destroying or removing material or components needed for the electro-active material to function properly.

16. The electro-active lens of claim 15 wherein a change in refractive index of the electro-active material is at least 0.02 units per volt.

* * * * *